US009603731B2

(12) United States Patent
Richter

(10) Patent No.: US 9,603,731 B2
(45) Date of Patent: Mar. 28, 2017

(54) HELICAL HYBRID STENT

(71) Applicant: MEDINOL LTD., Tel Aviv (IL)

(72) Inventor: Jacob Richter, Arsuf (IL)

(73) Assignee: Medinol Ltd., Tel Aviv (IL)

( * ) Notice: Subject to any disclaimer, the term of this patent is extended or adjusted under 35 U.S.C. 154(b) by 0 days.

(21) Appl. No.: 13/786,631

(22) Filed: Mar. 6, 2013

(65) Prior Publication Data
US 2013/0245748 A1    Sep. 19, 2013

Related U.S. Application Data

(63) Continuation of application No. 13/467,800, filed on May 9, 2012, now Pat. No. 9,456,910, which is a (Continued)

(51) Int. Cl.
*A61F 2/88* (2006.01)
*A61F 2/90* (2013.01)
(Continued)

(52) U.S. Cl.
CPC .......... *A61F 2/88* (2013.01); *A61F 2/91* (2013.01); *A61L 31/022* (2013.01); *A61L 31/10* (2013.01);
(Continued)

(58) Field of Classification Search
CPC .......... A61F 2/88; A61F 2002/075; A61F 2220/0025; A61F 2220/0058;
(Continued)

(56) References Cited

U.S. PATENT DOCUMENTS 3,986,867 A   10/1976  Masumoto et al.
4,017,911 A    4/1977  Kafesjian et al.
(Continued)

FOREIGN PATENT DOCUMENTS

EP   0 480 667 A1   4/1992
EP   2 526 905 A1   11/2012
(Continued)

OTHER PUBLICATIONS

European Search Report dated Dec. 2, 2003, 5 pages from related abandoned Application No. 01125340.8.
(Continued)

*Primary Examiner* — Christian Sevilla
*Assistant Examiner* — Seema Mathew
(74) *Attorney, Agent, or Firm* — Cadwalder Wickersham & Taft LLP

(57) ABSTRACT

An expandable helical stent is provided, wherein the stent may be formed of an amorphous metal alloy or other non-amorphous metal with a securement. The stent is formed from flat or tubular metal in a helical coiled structure which has an undulating pattern. The main stent component may be formed of a single helically coiled component. Alternatively, a plurality of helically coiled ribbons may be used to form a stent heterogeneous in design, material, or other characteristic particular to that stent. The helical tubular structure may be secured with a securement, such as a weld, interlock or a polymer, to maintain the helical coils in a tubular configuration. The helical coils of the main stent component may be spaced apart or nestled to each other. The nestling of the undulation of adjacent helical coils contributes to maintaining the tubular shape of the helically coiled stent. In addition, the nestling of helical coils may prevent the polymer layer from sagging at any point between cycles of the helical coils.

25 Claims, 7 Drawing Sheets

Related U.S. Application Data continuation of application No. 12/428,347, filed on Apr. 22, 2009, now Pat. No. 8,382,821, which is a continuation-in-part of application No. 11/377,769, filed on Mar. 15, 2006, which is a continuation-in-part of application No. 11/331,639, filed on Jan. 13, 2006, which is a continuation-in-part of application No. 10/860,735, filed on Jun. 3, 2004, now abandoned, said application No. 11/377,769 is a continuation-in-part of application No. 10/607,604, filed on Jun. 27, 2003, now abandoned.

(51) Int. Cl.
- A61F 2/91 (2013.01)
- A61L 31/02 (2006.01)
- A61L 31/10 (2006.01)
- A61F 2/07 (2013.01)
- A61F 2/89 (2013.01)

(52) U.S. Cl.
CPC ........... A61F 2/89 (2013.01); A61F 2002/075 (2013.01); A61F 2220/0025 (2013.01); A61F 2220/0058 (2013.01); A61F 2230/0091 (2013.01); A61F 2250/0068 (2013.01); Y10T 29/49764 (2015.01)

(58) Field of Classification Search
CPC ...... A61F 2230/0091; A61F 2250/0068; A61F 2/89; A61F 2/91
USPC ................................................ 623/1.16, 1.22
See application file for complete search history.

(56) References Cited

U.S. PATENT DOCUMENTS

| | | |
|---|---|---|
| 4,142,571 A | 3/1979 | Narasimhan |
| 4,144,058 A | 3/1979 | Chen et al. |
| 4,185,383 A | 1/1980 | Heimke et al. |
| 4,281,706 A | 8/1981 | Liebermann et al. |
| 4,409,041 A | 10/1983 | Datta et al. |
| 4,440,585 A | 4/1984 | Kanehira |
| 4,473,401 A | 9/1984 | Masumoto et al. |
| 4,481,001 A | 11/1984 | Graham et al. |
| 4,489,773 A | 12/1984 | Miller |
| 4,614,221 A | 9/1986 | Masumoto |
| 4,655,771 A | 4/1987 | Wallsten |
| 4,733,665 A | 3/1988 | Palmaz |
| 4,755,593 A | 7/1988 | Lauren |
| 4,760,849 A | 8/1988 | Kropf |
| 4,762,128 A | 8/1988 | Rosenbluth |
| 4,800,882 A | 1/1989 | Gianturco |
| 4,802,776 A | 2/1989 | Miyazawa et al. |
| 4,856,516 A | 8/1989 | Hillstead |
| 4,886,062 A | 12/1989 | Wiktor |
| 4,969,458 A | 11/1990 | Wiktor |
| 5,019,090 A | 5/1991 | Pinchuk |
| 5,037,377 A | 8/1991 | Alonso |
| 5,045,637 A | 9/1991 | Sato et al. |
| 5,102,417 A | 4/1992 | Palmaz |
| 5,104,404 A | 4/1992 | Wolff |
| 5,116,360 A | 5/1992 | Pinchuk et al. |
| 5,116,365 A | 5/1992 | Hillstead |
| 5,122,154 A | 6/1992 | Rhodes |
| 5,123,917 A | 6/1992 | Lee |
| 5,128,214 A | 7/1992 | Takayanagi et al. |
| 5,133,732 A | 7/1992 | Wiktor |
| 5,135,536 A | 8/1992 | Hillstead |
| 5,161,547 A | 11/1992 | Tower |
| 5,195,984 A | 3/1993 | Schatz |
| 5,282,824 A | 2/1994 | Gianturco |
| 5,292,331 A | 3/1994 | Boneau |
| 5,314,472 A | 5/1994 | Fontaine |
| 5,368,659 A | 11/1994 | Peker et al. |
| 5,370,683 A | 12/1994 | Fontaine |
| 5,381,856 A | 1/1995 | Fujikura et al. |
| 5,383,892 A | 1/1995 | Cardon et al. |
| 5,393,594 A | 2/1995 | Koyfman et al. |
| 5,405,377 A | 4/1995 | Cragg |
| 5,421,919 A | 6/1995 | Roman |
| 5,443,496 A | 8/1995 | Schwartz et al. |
| 5,449,373 A | 9/1995 | Pinchasik et al. |
| 5,464,438 A | 11/1995 | Menaker |
| 5,510,077 A | 4/1996 | Dinh et al. |
| 5,514,176 A | 5/1996 | Bosley |
| 5,527,337 A | 6/1996 | Stack et al. |
| 5,549,663 A | 8/1996 | Cottone et al. |
| 5,554,181 A | 9/1996 | Das |
| 5,554,182 A | 9/1996 | Dinh et al. |
| 5,556,413 A | 9/1996 | Lam |
| 5,562,729 A | 10/1996 | Purdy et al. |
| 5,571,166 A | 11/1996 | Dinh et al. |
| 5,575,818 A | 11/1996 | Pinchuk |
| 5,591,197 A | 1/1997 | Orth et al. |
| 5,591,198 A | 1/1997 | Boyle et al. |
| 5,591,223 A | 1/1997 | Lock et al. |
| 5,591,224 A | 1/1997 | Schwartz et al. |
| 5,595,571 A | 1/1997 | Jaffe et al. |
| 5,603,721 A | 2/1997 | Lau et al. |
| 5,609,627 A | 3/1997 | Goicoechea et al. |
| 5,618,299 A | 4/1997 | Khosravi et al. |
| 5,626,604 A | 5/1997 | Cottone |
| 5,628,785 A | 5/1997 | Scwartz et al. |
| 5,632,771 A | 5/1997 | Boatman et al. |
| 5,636,641 A | 6/1997 | Fariabi |
| 5,653,747 A | 8/1997 | Dereume |
| 5,672,169 A | 9/1997 | Verbeek |
| 5,674,278 A | 10/1997 | Boneau |
| 5,693,084 A | 12/1997 | Chuter et al. |
| 5,693,085 A | 12/1997 | Buirge et al. |
| 5,696,207 A | 12/1997 | Vargo et al. |
| 5,716,396 A | 2/1998 | Williams, Jr. |
| 5,720,776 A | 2/1998 | Chuter et al. |
| 5,720,777 A | 2/1998 | Jaffe et al. |
| 5,723,003 A | 3/1998 | Winston et al. |
| 5,725,573 A | 3/1998 | Dearnaley et al. |
| 5,728,150 A | 3/1998 | McDonald et al. |
| 5,733,303 A | 3/1998 | Israel et al. |
| 5,755,781 A | 5/1998 | Jayaraman |
| 5,769,884 A | 6/1998 | Solovay |
| 5,779,732 A | 7/1998 | Amundson |
| 5,782,905 A | 7/1998 | Richter |
| 5,788,626 A | 8/1998 | Thompson |
| 5,797,443 A | 8/1998 | Lin et al. |
| 5,800,456 A | 9/1998 | Maeda et al. |
| 5,800,507 A | 9/1998 | Scwartz et al. |
| 5,800,508 A | 9/1998 | Goicoechea et al. |
| 5,800,509 A | 9/1998 | Boneau |
| 5,807,404 A | 9/1998 | Richter |
| 5,810,872 A * | 9/1998 | Kanesaka et al. ........... 623/1.15 |
| 5,817,152 A | 10/1998 | Birdsall et al. |
| 5,824,037 A | 10/1998 | Fogarty et al. |
| 5,824,046 A | 10/1998 | Smith et al. |
| 5,824,052 A | 10/1998 | Khosravi et al. |
| 5,836,964 A | 11/1998 | Richter et al. |
| 5,836,966 A | 11/1998 | St. Germain |
| 5,843,120 A | 12/1998 | Israel et al. |
| 5,843,180 A | 12/1998 | Jaffe et al. |
| 5,843,181 A | 12/1998 | Jaffe et al. |
| 5,849,034 A | 12/1998 | Schwartz |
| 5,851,228 A | 12/1998 | Pinheiro |
| 5,855,597 A | 1/1999 | Jayaraman |
| 5,855,600 A | 1/1999 | Alt |
| 5,865,723 A | 2/1999 | Love |
| 5,879,381 A | 3/1999 | Moriuchi et al. |
| 5,879,382 A | 3/1999 | Boneau |
| 5,891,190 A | 4/1999 | Boneau |
| 5,891,191 A | 4/1999 | Stinson |
| 5,895,407 A | 4/1999 | Jayaraman |
| 5,895,419 A | 4/1999 | Tweden et al. |
| 5,899,934 A | 5/1999 | Amundson et al. |
| 5,902,332 A | 5/1999 | Schatz |
| 5,913,895 A | 6/1999 | Burpee et al. |

(56) References Cited

U.S. PATENT DOCUMENTS

| | | |
|---|---|---|
| 5,913,897 A | 6/1999 | Corso et al. |
| 5,922,020 A | 7/1999 | Klein et al. |
| 5,922,021 A | 7/1999 | Jang |
| 5,925,061 A | 7/1999 | Ogi et al. |
| 5,928,279 A | 7/1999 | Shannon et al. |
| 5,931,867 A | 8/1999 | Haindl |
| 5,938,697 A | 8/1999 | Killion et al. |
| 5,955,145 A | 9/1999 | Kalvala et al. |
| 5,964,770 A | 10/1999 | Flomenblit et al. |
| 5,997,575 A | 12/1999 | Whitson et al. |
| 5,997,973 A | 12/1999 | Bianca, Jr. |
| 6,010,530 A | 1/2000 | Goicoechea |
| 6,013,091 A | 1/2000 | Ley et al. |
| 6,013,854 A * | 1/2000 | Moriuchi ............ A61F 2/91 606/194 |
| 6,017,365 A | 1/2000 | Von Oepen |
| 6,027,525 A | 2/2000 | Suh et al. |
| 6,027,527 A | 2/2000 | Asano et al. |
| 6,042,605 A | 3/2000 | Martin et al. |
| 6,053,941 A | 4/2000 | Lindberg et al. |
| 6,059,808 A | 5/2000 | Boussignac et al. |
| 6,080,192 A | 6/2000 | Demopulos et al. |
| 6,096,070 A | 8/2000 | Ragheb et al. |
| 6,120,534 A | 9/2000 | Ruiz |
| 6,120,847 A | 9/2000 | Yang et al. |
| 6,132,461 A | 10/2000 | Thompson |
| 6,139,573 A | 10/2000 | Sogard et al. |
| 6,159,237 A | 12/2000 | Alt et al. |
| 6,159,239 A | 12/2000 | Greenhalgh |
| 6,162,537 A | 12/2000 | Martin et al. |
| 6,179,868 B1 | 1/2001 | Burpee et al. |
| 6,183,353 B1 | 2/2001 | Frantzen |
| 6,187,034 B1 | 2/2001 | Frantzen |
| 6,187,095 B1 | 2/2001 | Labrecque et al. |
| 6,190,403 B1 | 2/2001 | Fischell et al. |
| 6,190,406 B1 | 2/2001 | Duerig et al. |
| 6,190,407 B1 | 2/2001 | Ogle et al. |
| 6,193,747 B1 | 2/2001 | Von Oepen |
| 6,197,048 B1 | 3/2001 | Richter |
| 6,197,049 B1 | 3/2001 | Shaolian et al. |
| 6,221,098 B1 | 4/2001 | Wilson et al. |
| 6,224,625 B1 | 5/2001 | Jayaraman |
| 6,231,598 B1 | 5/2001 | Berry et al. |
| 6,238,401 B1 | 5/2001 | Richter |
| 6,240,615 B1 | 6/2001 | Kimes et al. |
| 6,241,762 B1 | 6/2001 | Shanley |
| 6,251,059 B1 | 6/2001 | Apple et al. |
| 6,251,134 B1 | 6/2001 | Alt et al. |
| 6,258,116 B1 | 7/2001 | Hojeibane |
| 6,258,117 B1 | 7/2001 | Camrud et al. |
| 6,264,689 B1 | 7/2001 | Colgan et al. |
| 6,273,910 B1 | 8/2001 | Limon |
| 6,287,333 B1 | 9/2001 | Appling et al. |
| 6,299,604 B1 | 10/2001 | Ragheb et al. |
| 6,299,755 B1 | 10/2001 | Richter |
| 6,309,411 B1 | 10/2001 | Lashinski et al. |
| 6,312,459 B1 | 11/2001 | Huang et al. |
| 6,315,794 B1 | 11/2001 | Richter |
| 6,319,277 B1 | 11/2001 | Rudnick et al. |
| 6,331,188 B1 | 12/2001 | Lau et al. |
| 6,334,868 B1 | 1/2002 | Ham |
| 6,340,367 B1 | 1/2002 | Stinson et al. |
| 6,344,053 B1 | 2/2002 | Boneau |
| 6,348,065 B1 | 2/2002 | Brown et al. |
| 6,355,039 B1 | 3/2002 | Troussel et al. |
| 6,355,059 B1 | 3/2002 | Richter et al. |
| 6,364,904 B1 * | 4/2002 | Smith ............ A61F 2/07 623/1.13 |
| 6,383,213 B2 | 5/2002 | Wilson et al. |
| 6,387,120 B2 | 5/2002 | Wilson et al. |
| 6,398,803 B1 | 6/2002 | Layne |
| 6,409,753 B1 | 6/2002 | Brown et al. |
| 6,416,538 B1 | 7/2002 | Ley et al. |
| 6,428,569 B1 | 8/2002 | Brown |
| 6,440,162 B1 | 8/2002 | Cox et al. |
| 6,464,719 B2 | 10/2002 | Jayaraman |
| 6,471,980 B2 | 10/2002 | Sirhan et al. |
| 6,478,815 B1 | 11/2002 | Alt |
| 6,485,508 B1 | 11/2002 | McGuinness |
| 6,503,270 B1 | 1/2003 | Richter et al. |
| 6,505,654 B1 | 1/2003 | Andersen et al. |
| 6,506,211 B1 | 1/2003 | Skubitz et al. |
| 6,506,408 B1 | 1/2003 | Palasis |
| 6,511,505 B2 | 1/2003 | Cox et al. |
| 6,527,801 B1 | 3/2003 | Dutta |
| 6,530,934 B1 | 3/2003 | Jacobsen et al. |
| 6,530,950 B1 | 3/2003 | Alvarado et al. |
| 6,540,774 B1 | 4/2003 | Cox |
| 6,540,775 B1 | 4/2003 | Fischell et al. |
| 6,558,414 B2 | 5/2003 | Layne |
| 6,562,065 B1 | 5/2003 | Shanley |
| 6,565,507 B2 | 5/2003 | Kamata et al. |
| 6,569,180 B1 | 5/2003 | Sirhan et al. |
| 6,579,310 B1 | 6/2003 | Cox et al. |
| 6,579,314 B1 | 6/2003 | Lombardi |
| 6,602,226 B1 | 8/2003 | Smith et al. |
| 6,602,281 B1 | 8/2003 | Klein |
| 6,602,282 B1 | 8/2003 | Yang et al. |
| 6,605,107 B1 | 8/2003 | Klein |
| 6,607,554 B2 | 8/2003 | Dang et al. |
| 6,610,086 B1 * | 8/2003 | Kock et al. ............ 623/1.22 |
| 6,638,301 B1 | 10/2003 | Chandrasekaran et al. |
| 6,645,237 B2 | 11/2003 | Klumb et al. |
| 6,645,240 B2 | 11/2003 | Yee |
| 6,648,911 B1 | 11/2003 | Sirhan et al. |
| 6,656,218 B1 | 12/2003 | Denardo et al. |
| 6,656,220 B1 | 12/2003 | Gomez et al. |
| 6,663,661 B2 | 12/2003 | Boneau |
| 6,663,664 B1 | 12/2003 | Pacetti |
| 6,673,102 B1 | 1/2004 | Vonesh et al. |
| 6,673,106 B2 | 1/2004 | Mitelberg et al. |
| 6,699,278 B2 | 3/2004 | Fischell et al. |
| 6,706,061 B1 | 3/2004 | Fischell et al. |
| 6,709,453 B2 | 3/2004 | Pinchasik et al. |
| 6,723,119 B2 * | 4/2004 | Pinchasik ............ A61F 2/91 623/1.15 |
| 6,730,117 B1 | 5/2004 | Tseng et al. |
| 6,733,536 B1 | 5/2004 | Gellman |
| 6,736,844 B1 | 5/2004 | Glatt et al. |
| 6,767,418 B1 | 7/2004 | Zhang et al. |
| 6,770,087 B2 | 8/2004 | Layne |
| 6,790,298 B2 | 9/2004 | Johnson et al. |
| 6,827,733 B2 | 12/2004 | Boneau |
| 6,863,757 B2 | 3/2005 | Gonzalez et al. |
| 6,866,805 B2 | 3/2005 | Hong et al. |
| 6,866,860 B2 | 3/2005 | Nathan |
| 6,899,727 B2 | 5/2005 | Armstrong et al. |
| 6,911,040 B2 | 6/2005 | Johnson |
| 6,962,604 B2 | 11/2005 | Hijlkema |
| 7,060,093 B2 | 6/2006 | Dang et al. |
| 7,108,714 B1 | 9/2006 | Becker |
| 7,112,293 B2 | 9/2006 | Dubson et al. |
| 7,163,555 B2 | 1/2007 | Dinh |
| 7,176,344 B2 | 2/2007 | Gustafson et al. |
| 7,185,677 B2 | 3/2007 | Houston et al. |
| 7,244,116 B2 | 7/2007 | Dubson et al. |
| 7,329,277 B2 | 2/2008 | Addonizio et al. |
| 7,360,542 B2 | 4/2008 | Nelson et al. |
| 7,441,559 B2 | 10/2008 | Nelson et al. |
| 7,540,881 B2 | 6/2009 | Meyer et al. |
| 7,637,939 B2 | 12/2009 | Tischler |
| 7,722,578 B2 | 5/2010 | Arney et al. |
| 7,722,661 B2 | 5/2010 | Lenz et al. |
| 7,846,198 B2 | 12/2010 | Hogendijk |
| 7,887,584 B2 | 2/2011 | Richter |
| 7,901,448 B2 | 3/2011 | Leopold et al. |
| 7,914,568 B2 | 3/2011 | Cully et al. |
| 7,922,756 B2 | 4/2011 | Lenz et al. |
| 7,955,387 B2 | 6/2011 | Richter |
| 8,236,043 B2 | 8/2012 | Caro et al. |
| 8,328,865 B2 | 12/2012 | Bales et al. |
| 8,460,364 B2 | 6/2013 | Cottone et al. |
| 8,496,703 B2 | 7/2013 | Richter |
| 2001/0020184 A1 | 9/2001 | Dehdashtian et al. |

(56) References Cited

U.S. PATENT DOCUMENTS

| | | |
|---|---|---|
| 2001/0032009 A1 | 10/2001 | Layne et al. |
| 2001/0044647 A1 | 11/2001 | Pinchuk et al. |
| 2001/0056298 A1 | 12/2001 | Brown et al. |
| 2002/0004677 A1 | 1/2002 | Jayaraman |
| 2002/0007212 A1 | 1/2002 | Brown et al. |
| 2002/0046783 A1 | 4/2002 | Johnson et al. |
| 2002/0049488 A1 | 4/2002 | Boneau |
| 2002/0049489 A1 | 4/2002 | Herweck et al. |
| 2002/0049492 A1 | 4/2002 | Lashinski et al. |
| 2002/0052649 A1 | 5/2002 | Greenhalgh |
| 2002/0055770 A1 | 5/2002 | Doran et al. |
| 2002/0068969 A1 | 6/2002 | Shanley et al. |
| 2002/0081732 A1 | 6/2002 | Bowlin et al. |
| 2002/0082680 A1 | 6/2002 | Shanley et al. |
| 2002/0082682 A1 | 6/2002 | Barclay et al. |
| 2002/0084178 A1 | 7/2002 | Dubson et al. |
| 2002/0103529 A1 | 8/2002 | Pinchasik et al. |
| 2002/0107560 A1 | 8/2002 | Richter |
| 2002/0116044 A1 | 8/2002 | Cottone et al. |
| 2002/0116049 A1 | 8/2002 | Girton et al. |
| 2002/0120327 A1 | 8/2002 | Cox et al. |
| 2002/0138136 A1 | 9/2002 | Chandresekaran et al. |
| 2002/0161319 A1 | 10/2002 | Matsumoto et al. |
| 2002/0162605 A1 | 11/2002 | Horton, Jr. et al. |
| 2002/0165603 A1* | 11/2002 | Thornton et al. ............ 623/1.13 |
| 2002/0177893 A1 | 11/2002 | Brown et al. |
| 2003/0017208 A1 | 1/2003 | Ignatious et al. |
| 2003/0028245 A1 | 2/2003 | Barclay et al. |
| 2003/0040803 A1 | 2/2003 | Rioux et al. |
| 2003/0045926 A1 | 3/2003 | Pinchasik |
| 2003/0050691 A1 | 3/2003 | Shifrin et al. |
| 2003/0069633 A1 | 4/2003 | Richter et al. |
| 2003/0083646 A1 | 5/2003 | Sirhan et al. |
| 2003/0100955 A1 | 5/2003 | Greenawalt et al. |
| 2003/0120197 A1 | 6/2003 | Kaneko et al. |
| 2003/0130721 A1 | 7/2003 | Martin et al. |
| 2003/0208260 A1 | 11/2003 | Lau et al. |
| 2003/0211135 A1 | 11/2003 | Greenhalgh et al. |
| 2003/0212449 A1 | 11/2003 | Cox |
| 2004/0013834 A1 | 1/2004 | Bonk et al. |
| 2004/0044401 A1 | 3/2004 | Bales et al. |
| 2004/0064180 A1 | 4/2004 | Boneau |
| 2004/0072124 A1 | 4/2004 | Kaufman et al. |
| 2004/0082989 A1 | 4/2004 | Cook et al. |
| 2004/0088043 A1 | 5/2004 | Klein |
| 2004/0098095 A1 | 5/2004 | Burnside |
| 2004/0102833 A1 | 5/2004 | Girton et al. |
| 2004/0106980 A1 | 6/2004 | Solovay et al. |
| 2004/0193251 A1 | 9/2004 | Rudnick et al. |
| 2004/0199242 A1 | 10/2004 | Hong et al. |
| 2004/0230291 A1 | 11/2004 | Richter |
| 2004/0236402 A1 | 11/2004 | Layne |
| 2004/0254419 A1 | 12/2004 | Wang et al. |
| 2004/0255096 A1 | 12/2004 | Norman |
| 2004/0260401 A1 | 12/2004 | Crawley et al. |
| 2004/0267349 A1 | 12/2004 | Richter |
| 2005/0033399 A1 | 2/2005 | Richter |
| 2005/0084407 A1 | 4/2005 | Myrick |
| 2005/0107864 A1 | 5/2005 | Hong et al. |
| 2005/0113888 A1 | 5/2005 | Jimenez et al. |
| 2005/0131515 A1 | 6/2005 | Cully et al. |
| 2005/0182483 A1 | 8/2005 | Osborne et al. |
| 2005/0209679 A1 | 9/2005 | Melsheimer |
| 2005/0216076 A1 | 9/2005 | Kveen et al. |
| 2005/0246010 A1 | 11/2005 | Alexander et al. |
| 2005/0261758 A1 | 11/2005 | Rourke et al. |
| 2005/0278019 A1 | 12/2005 | Gregorich |
| 2006/0030934 A1 | 2/2006 | Hogendijk et al. |
| 2006/0122691 A1 | 6/2006 | Richter |
| 2006/0149386 A1 | 7/2006 | Clarke et al. |
| 2006/0178727 A1 | 8/2006 | Richter |
| 2006/0195177 A1 | 8/2006 | Kaufmann et al. |
| 2006/0246210 A1 | 11/2006 | Iki et al. |
| 2007/0026132 A1 | 2/2007 | Williams et al. |
| 2007/0073383 A1 | 3/2007 | Yip et al. |
| 2007/0150046 A1 | 6/2007 | Meyer et al. |
| 2007/0208409 A1* | 9/2007 | Quigley ...................... 623/1.13 |
| 2007/0219618 A1 | 9/2007 | Cully et al. |
| 2007/0219642 A1 | 9/2007 | Richter |
| 2007/0239264 A1 | 10/2007 | Fliedner |
| 2007/0250148 A1 | 10/2007 | Perry et al. |
| 2007/0269936 A1 | 11/2007 | Tanaka et al. |
| 2008/0097582 A1 | 4/2008 | Shanley et al. |
| 2008/0215129 A1 | 9/2008 | Venturelli et al. |
| 2008/0221664 A1 | 9/2008 | Bales et al. |
| 2008/0319534 A1 | 12/2008 | Birdsall et al. |
| 2008/0319535 A1 | 12/2008 | Craven et al. |
| 2009/0012525 A1 | 1/2009 | Buehlmann et al. |
| 2009/0036976 A1 | 2/2009 | Beach et al. |
| 2009/0062903 A1 | 3/2009 | Pathak |
| 2009/0210049 A1 | 8/2009 | Thielen et al. |
| 2009/0234433 A1 | 9/2009 | Richter |
| 2009/0259294 A1 | 10/2009 | Cully et al. |
| 2009/0264986 A1 | 10/2009 | Bales et al. |
| 2009/0306766 A1 | 12/2009 | McDermott et al. |
| 2010/0004725 A1 | 1/2010 | Zipse et al. |
| 2010/0016949 A1 | 1/2010 | Wack |
| 2010/0070024 A1 | 3/2010 | Venturelli et al. |
| 2010/0198333 A1 | 8/2010 | Macatangay et al. |
| 2010/0256735 A1 | 10/2010 | Morales, Jr. |
| 2011/0004290 A1 | 1/2011 | Bales et al. |
| 2011/0125251 A1 | 5/2011 | Cottone et al. |
| 2011/0166641 A1 | 7/2011 | Bales et al. |
| 2011/0184507 A1 | 7/2011 | Fischer, Jr. et al. |
| 2011/0208288 A1 | 8/2011 | Arbefeuille et al. |
| 2011/0218615 A1 | 9/2011 | Griswold |
| 2011/0251668 A1 | 10/2011 | Thompson et al. |
| 2012/0265288 A1 | 10/2012 | Jones et al. |
| 2012/0303112 A1 | 11/2012 | Armstrong et al. |
| 2013/0090721 A1 | 4/2013 | Bales et al. |
| 2013/0306364 A1 | 11/2013 | Suzuki et al. |
| 2014/0135904 A1 | 5/2014 | Rowe |
| 2014/0358218 A1 | 12/2014 | Mitsudo et al. |
| 2014/0379066 A1 | 12/2014 | Burpee et al. |
| 2015/0045874 A1 | 2/2015 | McMahon et al. |
| 2015/0250271 A1 | 9/2015 | Ogilvie |

FOREIGN PATENT DOCUMENTS

| | | |
|---|---|---|
| EP | 2 529 706 A1 | 12/2012 |
| FR | 2 760 351 | 9/1998 |
| WO | WO 00/45743 | 8/2000 |
| WO | WO 00/76423 | 12/2000 |
| WO | WO 03/026713 | 4/2003 |
| WO | WO 2004/034931 | 4/2004 |
| WO | WO 2004/058100 | 7/2004 |
| WO | WO 2004/110302 | 12/2004 |
| WO | WO 2007/080510 | 7/2007 |
| WO | WO 2007/109007 A1 | 9/2007 |
| WO | WO 2008/117315 | 10/2008 |
| WO | WO 2010/027494 A1 | 3/2010 |

OTHER PUBLICATIONS

European Search Report dated Oct. 25, 2004, 5 pages from related abandoned Application No. 01125341.6.
European Search Report dated Mar. 11, 2005, 4 pages from related abandoned Application No. 02733008.3.
Supplemental European Search Report dated Sep. 5, 2007, 3 pages from related Application No. EP 04737140.
Supplemental European Search Report dated Aug. 31, 2009, 3 pages from related Application No. EP 07700481.
Extended EP Search Report, Application No. EP 09008421.1 dated Jan. 15, 2010.
Extended EP Search Report, Application No. EP09008420.3 dated Jan. 15, 2010.
Extended EP Search Report, Application No. EP 09008419.5 dated Jan. 15, 2010.
Extended EP Search Report, Application No. EP07733978.6 dated Mar. 17, 2010.
Extended European Search Report dated Jul. 7, 2010 for EP Application No. 10004585.5-1219, 7 pages.

(56) References Cited

OTHER PUBLICATIONS

EP Search Report dated Jul. 3, 2008, Application No. EP 1751363.
Extended EP Search Report, Publ No. EP 1996113 / App. No. EP 07733978.6dated Mar. 17, 2010.
International Search Report and Written Opinion dated Aug. 4, 2010 for PCT Application No. PCT/IB2010/001036, 13 pages.
PCT International Search Report, Application No. PCT/US98/19990 dated May 6, 1999.
PCT International Search Report and Written Opinion dated Apr. 5, 2005, 10 pages from related PCT Application No. PCT/IB04/02096.
PCT International Search Report dated May 9, 2009, Application No. PCT/IB05/01524 / Published No. WO 05/118971.
PCT International Search Report and Written Opinion dated Jun. 11, 2008, 9 pages from related Application No. PCT/IB2007/000088.
PCT International Search Report, Dec. 8, 2008, 7 pages, from co-pending PCT Application No. PCT/IB2007/000632.
International Preliminary Report on Patentability dated Feb. 25, 2010, 8 pages from related Application No. PCT/IB2008/002515.
PCT International Search Report and Written Opinion dated Dec. 3, 2009, 14 pages from related Application No. PCT/IB2008/002515.
GB Search Report under Section 17 of the 1977 Patent Act dated Apr. 8, 2004, 1 pages from related Application No. GB 0402845.2.
Translation of an OA issued by the German Patent and Trademark Office dated Feb. 28, 2008, Application No. DE 19956249.0-43.
Singapore Search and Examination Report dated Sep. 13, 2000, Application No. 9904228-8.
New Zealand Examination Report dated Sep. 8, 1999, Application No. 337652.
*BSC Cancellation Proceeding* v. *Medinol* DE 20108764, NIRflex dated Jan. 11, 2005.
*BSC Cancellation Proceeding* v. *Medinol* DE 20108765, NIRflex dated Jan. 11, 2005.
Horton et al., "Biomedical Potential of a Zirconium-Based Bulk Metallic Glass" Mat. Res. Soc. Symp. Proc. vol. 754, Materials Research Society, Feb. 14, 2003, http://www.ornl.gov/webworks/cppr/y2001/pres/116372.pdf.
Database WPI Week 20012 Derwent Publications Ltd., London GB; AN 2000-129595 XP002446760 / JP 20000-000297 A (Inoue A) Jan. 7, 2000.
Busch, R. et al., "On the Glass Forming Ability of Bulk Metallic Glass", Materials Science Forum vols. 235-238 (1997) pp. 327-336.
Cahn, R., "Atomic Transport in Amorphous Alloys: An Introduction", J.Vac. Sci, Technol. A (4(6), Nov./Dec. 1986.
Donaldson, J., "Metallic Glasses: A New Class of Electroplated Coatings", Surface Finishing, Jul. 1986.
Duwez, P. "A Typical Example of Metastability: Metallic Glasses", J.Vac. Sci. Technol. B1 (2) Apr.-Jun., 1983.
Fecht, H. et al., "Destabilization and Vitrification of Crystalline Matter", J. Non-Crystalline Solids, 117/118 (1990) 704-707.
Johnson, W.L. et al., "Electronic Structure of Metallic Glasses", Glassy Metals: Magnetic, Chemical, and Structural Properties, CRC press, pp. 65-108.
Johnson, W.L., "Fundamental Aspects of Bulk Metallic Glass formation in Multicomponent Assays", Materials Science Forum, vols. 225-227 (1996) pp. 35-50.
Johnson, W.L., "Bulk Metallic Glasses—A New Engineering Material", current Opinion in Solid State & Materials Science, 1996, 1:383-386.
Johnson, W.L., "Mechanisms of Instability in Crystalline Alloys with Respect to Vitrification", Journal of Less-Common Metals, 145 (1988) 63-80.
Kavesh, S., "Principles of Fabrication", Metallic Glasses, Papers presented at a Seminar of the Materials Science Division of the American Society for Metals, Sep. 18 and 19, 1976.
Kukulka, D., "New Chill-block Melt Spinning Relations to Predict Ribbon Thickness", J. Thermophysics, vol. 10, No. 3, Technical Notes, 1996.
Kung, K. T-Y., "Electrical Characteristics of Amorphous Molybdenum-Nickel Contacts to Silicon", J.Appl. Phys., 55(10), May 15, 1984 pp. 3882-3885.

Liebermann, H., et al., "Technology of Amorphous Alloys", ChemTech, Jun. 1987, pp. 363-367.
Liebermann, H.H., "The Dependence of the Geometry of Glassy Alloy Ribbons on the Chill Bock Melt-Spinning Process Parameters", Materials Science and Engineering, 43 (1980) 203-210.
Takayama, S., et al., "The Analysis of Casting Conditions of Amorphous Alloys", J. Appl. Phys. 50 (7), Jul. 1979, pp. 4962-4965.
Thakoor, A.P. et al., "Influence of the Microstructure on the Corrosion Behavior of Magnetron Sputter-Quenched Amorphous Metal Alloys", J. Vac. Sci. Technol. A 1 (2), Apr.-Jun. 1983, pp. 520-523.
Williams, R.M. et al., "Corrosion Behavior of Magnetron Sputter-Deposited $[Mo_{0.6}Ru_{0.4}]B_{18}$ and $Mo_{82}B_{18}$ Amorphous Metal Films", J. Electrochemical Soc., vol. 131 No. 12, pp. 2791-2794.
Zhu, M.F. et al., "Electrical Characteristics of Amorphous $Ni_{36}W_{64}$ Contacts on SI", Advanced Semiconductor Processing and Characterization of Electronic and Optical Materials, Proceedings of SPIE, vol. 463, Jan. 24-25, 1984.
Zhu, M. F., et al., "Investigation of Amorphous $W_{60}Zr_{40}$ Film as a Diffusion Barrier in Metallization Schemes", Phys. Stat. Sol. (a) S6, 471 (1984).
"Technology: Hot Alloy" [online]. Forbes Magazine, Sep. 30, 2002[retrieved Feb. 19, 2003] Retrieved from the internet: <URL:www.forbes.com/global/2002/0930/128.html>.
"Innovative Material is Stronger than Titanium but can be formed like a Plastic" [online]. Jobwerx Manufacturing Network. [retrieved Feb. 19, 2003]. Retrieved from the internet: <URL:www.jobwerx.com/news/archives/LiquidmetalAlloys.com>.
"Liquidmetal Medical Devices" [online], Liquidmetal Technologies, [retrieved Feb. 20, 2003]. Retrieved from the internet: <URL:www.liquidmetal.com/applications/dsp.medical.asp>.
"Liquidmetal Technology Reborn in LMG" [online]. Golfweb, Jul. 31, 2002 [retrieved Feb. 20, 2003]. Retrieved from the internet: <URL:www.golfweb.com/u/cd/multi/0,1977m5564401,00.html>.
"Choosing the right suture material" [online], The Royal College of Surgeons of Edinburgh [retrieved Mar. 5, 2003]. Retrieved from the internet <URL: www.edu.rcsed.ac.uk/lectures/1t5.htm>.
"BBC health—Ask the Doctor—Heart Valves Replacement" [online]. BBC health homepage, Jul. 18, 2001. [retrieved Mar. 12, 2003]. Retrieved from the internet: <URL: www.bbc.co.uk/health/ask_doctor/heartvalve_replacement.shtml>.
"Artificial Organs Cardiovascular" [online]. National University of Singapore. [retrieved Feb. 12, 2003]. Retrieved from the internet <URL: www.scholars.nus.edu.sg/cpace/prosthesis/stein/cardio.html>.
"Heart replacement valves" [online]. Research Defense Society. [retrieved Mar. 12, 2003]. Retrieved from the internet: <URL: www.rds-online.org.uk/milestones/valves.html>.
"Material considerations in Replacement Heart Valves" [online]. Rose-Hulman Institute of Technology Fall 1996 [retrieved Mar. 12, 2003]. Retrieved from the internet: <URL: www.rose-hulman.edu/class/scheme/HTML/SiteMap/Undergraduate/StudentProjects/MaterialsStudentProjects/heart/heart.html>.
"The Physics Behind Artificial Heart Valves" [online]. Claire Carson, et al., Dec. 4, 2000 [retrieved Mar. 12, 2003] Retrieved from the internet: <URL: www.ipass.net/~tonyg/HeartValvesWeb.html>.
"Medical Dictionary—Artificial Heart Valve" [online]. Dr. Malcolm C. Brown, 2000 [retrieved on Mar. 12, 2003]. Retrieved from the internet: <URL: http://www.thebrowns23.freeserve.co.uk/entries/ARTIFICIAL_HEART_VALVE>.
Jostent Peripheral Stent Graft [online]. JOMED 2002, [retrieved Mar. 14, 2003]. Retrieved from the internet: <URL:www.jomed.com/products/jpsg/productinfo/jostent-psg.html>.
"Recent Advances in Titanium Wire Technology", [online]. TP Orthodontics, Inc. Jan. 1999 [retrieved Mar. 15, 2003]. Retrieved from the internet: <URL:http://www.tportho.com/doctorsroom/whitepapers/pdf/titanium.pdf>.
"Dental Implants" [online]. Niagara Oral Surgery [retrieved on Mar. 17, 2003] <URL: www.niagaraoralsurgery.com/ser_implants.htm>.
"Lecture 11—Metals for Implantation", [online]. Wayne State University, [retrieved Mar. 17, 2003]. Retrieved from the internet: <URL:http://ttb.eng.wayne.edu/~grimm/BME5370/Lect11Out.html>.

(56) References Cited

OTHER PUBLICATIONS

"Investment Materials" [online]. Guy's, King's College & St. Thomas's Hospital Dental Institute, Dental Biomaterials Science, R.V. Curtis [retrieved Mar. 15, 2003]. Retrieved from the internet: <URL: http://r-curtis.umds.ac.uk/bds3a/investment%20materials%201.htm>.

"Metal Casting Alloys" [online]. Guy's, King's College & St. Thomas's Hospital Dental Institute, Dental Biomaterials Science, R.V. Curtis [retrieved on Mar. 15, 2003]. Retrieved from the internet: <URL: http://r-curtis.umds.ac.uk/bds3a/BMCalloys.HTM>.

"Metals & Alloys" [online]. Guy's, King's College & St. Thomas's Hospital Dental Institute, Dental Biomaterials Science, R.V. Curtis, [retrieved on Mar. 15, 2003]. Retrieved from the internet: <URL: http://r-curtis.umds.ac.uk/bds3a/metallurgy.HTM>.

"TP Original Wire: Development of a High-Performance Orthodontic Wire", [online]. TP Orthodontics, Inc. 1998 [retrieved on Mar. 15, 2003]. Retrieved from the internet: <URL: http://www.tportho.com.br/doctorsroom/whitepapers/pdf/originalwire.pdf>.

"Metallic Glasses Bulk Up", [online]. Mechanical Engineering Magazine, Jun. 1998. [retrieved on Mar. 21, 2003]. Retrieved from the internet: <URL:www.memagazine.org/backissues/june98/features/metallic/metallic.html>.

"Hasta La Vista, Titanium", [online]. Business 2.0, Oct. 2002. [retrieved on Mar. 21, 2003]. Retrieved from the internet: <URL:www.business2.com/articles/mag/print/0,1643,43538,00.html>.

"New metal alloy is super strong", [online]. You magazine. [retrieved on Mar. 21, 2003]. Retrieved on the internet: <URL:www.yo.com.au/news/1022.htm>.

"Lessons of the Björk-Shiley Heart Valve Failure, Mechanics of Heart Valves" [online]. University of Texas at Austin. [retrieved on Mar. 25, 2003]. Retrieved from the internet: <URL: www.me.utexas.edu/~uer/heartvalves/mechanics.html>.

Atzmon, M. et al., "Study of Amorphouse Phases Formed by Solid-State Reaction in Elemental Composites", Rapidly Quenched Metals, Proceedings of the Fifth International Conference on Rapidly Quenced Metals, Wüzburg, Germany, Sep. 3-7, 1984.

Office Actions and Responses to Office Actions of related co-pending U.S. Appl. No. 11/377,769 filed Mar. 15, 2006: Amendment and Response to Final Rejection with Request for Continued Examination dated Apr. 13, 2012; Final Rejection dated Jan. 13, 2012; Amendment and Response to Non-Final Rejection dated Nov. 30, 2011; Non-Final Rejection dated Aug. 1, 2011; Amendment and Response to Final Rejection with Request for Continued Examination dated Sep. 15, 2010; Final Rejection dated Jun. 15, 2010; Amendment and Response to Non-Final Rejection dated Mar. 24, 2010; Non-Final Rejection dated Dec. 24, 2009; Amendment and Response to Restriction Requirement Sep. 28, 2009; and Requirement for Restriction/Election dated Aug. 27, 2009.

Office Actions and Responses to Office Actions of related co-pending U.S. Appl. No. 12/428,347 filed Apr. 22, 2009: Notice of Allowance dated Oct. 2, 2012; Supplemental Amendment dated May 9, 2012; Amendment and Response to Non-Final Rejection dated Mar. 22, 2012; Non-Final Rejection dated Dec. 23, 2011; Examiner Interview Summary dated Jul. 21, 2011; and Non-Final Rejection dated Apr. 27, 2011.

Office Actions and Responses to Office Actions of related abandoned U.S. Appl. No. 10/860,735 filed Jun. 3, 2004: Notice of Abandonment dated Jun. 6, 2007; Examiner Interview Summary Record dated Apr. 4, 2007; Non-Final Rejection dated Oct. 11, 2006; Response to Election/Restriction Requirement with Extension of Time dated Aug. 11, 2006; and Requirement for Restriction/Election dated Apr. 11, 2006.

Office Actions and Responses to Office Actions of related co-pending U.S. Appl. No. 11/331,639 filed Jan. 13, 2006: Amendment and Response to Final Rejection with Request for Continued Examination dated Aug. 4, 2010; Examiner Interview Summary dated Jun. 29, 2010; Final Rejection dated May 4, 2010; and Amendment and Response to Non-Final Rejection with Extension of Time dated Feb. 2, 2010; Non-Final Rejection dated Sep. 2, 2009; RCE, Amendment after Final Office Action, and EOT dated Jun. 18, 2009; Advisory Action dated Jun. 17, 2009; Amendment after Final Office Action May 18, 2009; Final Rejection dated Feb. 18, 2009; Applicant Summary of Interview with Examiner dated Jan. 12, 2009; Examiner Interview Summary Records dated Dec. 5, 2008; Response to Election/Restriction Requirement dated Dec. 1, 2008; Requirement for Restriction/Election dated Oct. 31, 2008; Replacement Drawings under 37 CFR 1.121(d) filed Aug. 1, 2008; Examiner Interview Summary dated Jul. 29, 2008; Amendment and Response to Non-Final Rejection w/ EOT dated Jul. 28, 2008; Non-Final Rejection dated Jun. 30, 2008.

Office Actions and Response to Office Actions of related co-pending U.S. Appl. No. 11/729,516 filed Mar. 28, 2007: Application Initiated Interview Summary and Office Action Appendix dated May 4, 2012; Amendment and Response to Final Rejection with Request for Continued Examination dated May 1, 2012; Final Rejection dated Feb. 1, 2012; Amendment and Response to Non-Final Rejection dated Dec. 20, 2011; and Non-Final Rejection dated Sep. 20, 2011.

Office Actions and Responses to Office Actions of related co-pending U.S. Appl. No. 10/607,604 filed Jun. 27, 2003: Notice of Abandonment dated Jun. 4, 2009; Final Rejection dated Dec. 3, 2008; Amendment and Response to Non-Final Rejection with Extension of Time dated Nov. 13, 2007; Non-Final Rejection dated Jul. 12, 2007; Amendment and Response to Final Rejection with Request for Continued Examination & Extension of Time dated May 2, 2007; Final Rejection dated Nov. 6, 2006; Amendment and Response to Non-Final Rejection with Extension of Time dated Aug. 11, 2006; Non-Final Rejection dated May 1, 2006; Request for Continued Examination & Extension of Time dated Apr. 7, 2006; Advisory Action dated Mar. 31, 2006; Amendment and Response to Final Rejection dated Mar. 13, 2006; Final Rejection date Dec. 12, 2005; Amendment and Response to Notice of Non-Compliance dated Sep 15, 2005; Notice of Non-Compliant or Non-Responsive Amendment dated Aug. 24, 2005; Amendment and Response to Non-Final Rejection dated May 18, 2005; Non-Final Rejection dated Feb. 23, 2005; Response to Restriction Requirement dated Dec. 17, 2004; and Requirement for Restriction/Election dated Nov. 17, 2004.

Office Actions and Responses to Office Actions of related co-pending U.S. Appl. No. 12/243,723 filed Oct. 1, 2008: Notice of Allowances dated Nov. 24, 2010, Oct. 29, 2010 and Oct. 5, 2010; Amendment and Response to Final Rejection with Request for Continued Examination dated Jul. 7, 2010; Examiner Interview Summary Record dated Jun. 29, 2010; Final Rejection dated Apr. 7, 2010; Amendment and Response to Non-Final Rejection dated Dec. 18, 2009; and Non-Final Rejection dated Sep. 18, 2009.

Office Actions and Responses to Office Actions of related co-pending U.S. Appl. No. 12/243,732 filed Oct. 1, 2008: Notice of Abandonment dated Oct. 28, 2010; Examiner Interview Summary Record dated Jun. 29, 2010; Final Rejection dated Apr. 9, 2010; Amendment and Response to Non-Final Rejection with Extension of Time dated Jan. 20, 2010; and Non-Final Rejection dated Sep. 21, 2009.

Office Actions and Response to Office Actions of related U.S. Appl. No. 12/243,741 filed Oct. 1, 2008: Supplemental Notice of allowability dated May 9, 2011; Supplemental Notice of Allowability dated Apr. 29, 2011; Applicant Summary of Interview with Examiner dated Feb. 28, 2011; Notice of Allowance and Fees Due w/ Examiner Interview Summary Record dated Jan. 28, 2011; Amendment and Response to Non-Final Rejection dated Nov. 29, 2010; and Non-Final Rejection dated Sep. 30, 2010.

Office Actions and Responses to Office Acitons of related abandoned U.S. Appl. No. 09/204,830 filed Dec. 3, 1998: Notice of Abandonment dated Oct. 1, 2002; Request for Extension of Time dated Apr. 5, 2002; Final Rejection dated Dec. 11, 2001; Amendment and Response after Non-Final Rejection dated Oct. 10, 2001; Non-Final Rejection dated Sep. 10, 2001; Request for Continued Examination dated Jul. 27, 2001; Advisory Action dated Jul. 18, 2001; Amendment and Response after Final Rejection dated Jul. 11, 2001; Final Rejection dated May 11, 2001; Amendment and Response after Non-Final Rejection with Extension of Time dated Mar. 7, 2001; Non-Final Rejection dated Sep, 18, 2000; Continuing

(56) References Cited

OTHER PUBLICATIONS

Prosecution Application dated Aug. 16, 2000; Advisory Action dated Jul. 31, 2000; Amendment after Final Rejection dated Jul. 3, 2000; Final Rejection dated May 5, 2000; Response after Non-Final Rejection dated Jan. 31, 2000; and Non-Final Rejection dated Aug. 3, 1999.
Office Actions and Responses to Office Actions of related abandoned U.S. Appl. No. 10/116,159 filed Apr. 5, 2002: Notice of Abandonment dated Jan. 25, 2005; Advisory Action dated Jul. 20, 2004; Amendment and Response after Final Rejection dated Jun. 30, 2004; Final Rejection dated Jun. 8, 2004; Amendment and Response after Non-Final Rejection dated Mar. 24, 2004; Non-Final Rejection dated Dec. 1, 2003; Response to Restriction/Election Requirement dated Sep. 17, 2003; and Requirement for Restriction/Election dated Aug. 26, 2003.
Extended European Search Report from corresponding EP Application No. 12176459.1-2320 dated Oct. 31, 2012, 7 pages.
Extended European Search Report and Opinion from corresponding EP Application No. 1218199.1-2320 dated Oct. 1, 2012, 6 pages.
Extended European Search Report from corresponding EP Application No. 12187494.5-2320 dated Nov. 15, 2012, 6 pages.
Office Actions and Responses to Office Actions of related abandoned U.S. Appl. No. 13/096,561 filed Apr. 28, 2011: Final Rejection dated Feb. 11, 2013; Response to Non-Final Rejection and Terminal Disclaimer dated Nov. 16, 2012; and Non-Final Rejection dated Aug. 16, 2012.
Office Actions and Responses to Office Actions of related co-pending U.S. Appl. No. 12/764,418 filed Apr. 21, 2010: Amendment and Response to Non-Final Rejection with Replacement Drawings filed Feb. 27, 2013; and Non-Final Rejection dated Nov. 28, 2012.
International Search Report and Written Opinion from PCT Application No. PCT/IB2014/001121 dated Oct. 15, 2014, 11 pages.

\* cited by examiner

HELICAL HYBRID STENT

This application is a continuation of application Ser. No. 13/467,800, filed on May 9, 2012, which is a continuation of application Ser. No. 12/428,347, filed on Apr. 22, 2009, issued as U.S. Pat. No. 8,382,821 on Feb. 26, 2013, which is a continuation-in-part of application Ser. No. 11/377,769 filed on Mar. 15, 2006, which is a continuation-in-part of application Ser. No. 11/331,639, filed on Jan. 13, 2006, which is a continuation-in-part of application Ser. No. 10/860,735, filed on Jun. 3, 2004, now abandoned. Application Ser. No. 11/377,769 is also a continuation-in-part of application Ser. No. 10/607,604, filed on Jun. 27, 2003, now abandoned. The entirety of these priority applications is hereby incorporated in toto by reference.

FIELD OF THE INVENTION

The invention relates generally to stents, which are intraluminal endoprosthesis devices implanted into vessels within the body, such as blood vessels, to support and hold open the vessels, or to secure and support other endoprostheses in vessels.

BACKGROUND OF THE INVENTION

Various stents are known in the art. Typically, stents are generally tubular in shape, and are expandable from a relatively small, unexpanded diameter to a larger, expanded diameter. For implantation, the stent is typically mounted on the end of a catheter with the stent being held on the catheter in its relatively small, unexpanded diameter. Using a catheter, the unexpanded stent is directed through the lumen to the intended implantation site. Once the stent is at the intended implantation site, it is expanded, typically either by an internal force, for example by inflating a balloon on the inside of the stent, or by allowing the stent to self-expand, for example by removing a sleeve from around a self-expanding stent, allowing the stent to expand outwardly. In either case, the expanded stent resists the tendency of the vessel to narrow, thereby maintaining the vessel's patency.

Stents may be constructed from tubes or from a flat sheet of metal, which is rolled and fixed such as in welding, mechanical lock or otherwise, to form the tubular structure of the stent.

Some examples of patents relating to stent designs include U.S. Pat. No. 4,733,665 to Palmaz; U.S. Pat. Nos. 4,800,882 and 5,282,824 to Gianturco; U.S. Pat. Nos. 4,856,516 and 5,116,365 to Hillstead; U.S. Pat. Nos. 4,886,062 and 4,969,458 to Wiktor; U.S. Pat. No. 5,019,090 to Pinchuk; U.S. Pat. No. 5,102,417 to Palmaz and Schatz; U.S. Pat. No. 5,104,404 to Wolff; U.S. Pat. No. 5,161,547 to Tower; U.S. Pat. No. 5,383,892 to Cardon et al.; U.S. Pat. No. 5,449,373 to Pinchasik et al.; and U.S. Pat. No. 5,733,303 to Israel et al.

One type of stent is known as the helical or coiled stent. Such a stent design is described in, for example, U.S. Pat. Nos. 6,503,270 and 6,355,059, which are incorporated herein, in toto, by reference. This stent design is configured as a helical stent in which the coil is formed from a wound strip of cells wherein the cells form a serpentine pattern comprising a series of bends. Other similar helically coiled stent structures are known in the art.

One object of prior stent designs has been to insure that the stent has sufficient radial strength when it is expanded so that it can sufficiently support the lumen. Stents with high radial strength, however, tend also to have a higher longitudinal rigidity than the vessel in which it is implanted. When the stent has a higher longitudinal rigidity than the vessel in which it is implanted, increased trauma to the vessel may occur at the ends of the stent, due to stress concentrations on account of the mismatch in compliance between the stented and un-stented sections of the vessel, or otherwise, the rigid stent may interfere with the vessel's natural tendency to bend and to stretch. Conversely, stents with good flexibility often lack sufficient and/or uniform radial support for the vessel wall. Thus, a continued need exists in the art for a stent having a balance of good radial strength and a high degree of longitudinal flexibility.

Another problem in the art arises when trying to simplify the manufacturing process of a stent to reduce costs yet prevent manufacturing defects, while still producing a stent with uniformly high flexibility and sufficient radial support.

SUMMARY OF THE INVENTION

The present invention provides a helical stent that is longitudinally flexible such that it can easily be tracked down tortuous lumens and does not significantly change the compliance of the vessel after deployment, wherein the stent is relatively stable so that it avoids bending or tilting in a manner that would potentially obstruct the lumen and avoids leaving significant portions of the vessel wall unsupported. The stent of the present invention comprises a helical structure maintained by a polymer fiber layer or other securement. Further, this stent has the radial support of a metal stent combined with longitudinal flexibility, conformability and fatigue resistance to longitudinal repeated bending, compression and twisting, that is much higher than that achievable by metal stents.

One embodiment of the invention comprises a main stent component combined with a polymer fiber layer such as, for example, a biocompatible material, wherein the polymer fiber layer maintains the tubular shape of the stent while the main component provides structural support both to the vessel and the polymer fiber layer to prevent sagging of the polymer layer into the lumen upon deployment.

The main stent component may be formed of a ribbon or strip as a continuous elongated component, preferably having spaced undulating portions forming periodic loop portions. The undulating portions are understood to include portions having a generally sinusoidal or zig-zag pattern. The ribbon may be helically wound to produce a helical, tubular structure which can function to hold open a blood vessel upon expansion. The ribbon is designed so as to naturally form a helical, tubular structure upon helical winding such that the individual cycles of the helical coils—defined by the length of the ribbon required to traverse the entire circumference of the resulting tubular structure in the helical direction—are spaced apart from one another across the longitudinal axis of the tubular structure. The stent can also comprise two or more simultaneously wound ribbons, such that the windings of the different ribbons will interchange or alternate along the stent or will be partially or completely overlapped.

Alternatively, the main stent component or helically oriented ribbon may be formed from a tube wherein the tubular structure has been etched or laser cut into the helically coiled structure of the instant invention.

The main stent component forms a tubular structure of helical coils. The distance along the longitudinal axis of the stent between cycles of the helical coils may vary in length depending on the needs of the particular stent.

In another embodiment, the main stent component may be designed such that each undulating coil directly abuts an adjacent undulating coil of the helical structure so that the space between cycles is minimized; that is, the undulating pattern is nestled into an adjacent, substantially similar undulating pattern at different cycles of the helical coils. In this manner, the helical coils of the stent provide enhanced coverage of the wall of the lumen without loss of overall stent flexibility. Because the helical coils may be nestled into one another without directly touching each other, the overall flexibility of the formed stent is unaffected by the proximity of different cycles of the helical coils. This arrangement also prevents potential sagging of the polymer layer connecting the helix. The nestling of elements in adjacent coils can be either by nestling of undulating structures as described above or by nestling of any type of connected elements, connected to the undulating structure. These elements can be straight—stick like—elements aligned with the longitudinal direction of the stent or slanted or curved relative to it.

The main stent component may comprise side bands and end bands. The side bands extend in a parallel fashion along the length of the main stent component. Each preferably comprises an undulating pattern which may intersect directly with one or more adjacent side bands or through cross-struts. End bands may extend from either end of the strip and are positioned at an angle to the side bands which form the central portion of the ribbon. These end bands may be designed to form a circumferential band or ring around the circumference of the tubular structure at either or both ends of the stent upon formation. The end bands may be tapered and/or affixed with additional elements, such as hooks, polymers, welds or the like to secure the ends of the helical tubular structure.

The main stent component may be formed from amorphous metal alloys, regular metals, or other biocompatible materials. Amorphous metal stents of the invention may be formed of one or more flat sheets of helically wound metal. Because amorphous metal alloys cannot be easily welded without the metal reverting to an undesirable crystalline form, the present invention contemplates wrapping or embedding the helically coiled amorphous metal alloy main stent component in a polymer fiber layer, such as a biocompatible non-metallic material, thereby forming a hybrid stent, where hybrid is taken to mean that the mechanical properties of the stent are a hybrid of a strong radial structure typical for metal and soft, flexible and durable longitudinal structure typical of non-metallic materials.

In one embodiment, the main stent component may be held in its helical coiled form by a polymer layer without requiring welding or otherwise interlocking the helically wound strip to itself. In another embodiment, the main stent component is held in its helical form by welding or interlocking elements of the helical coils to hold the structure in proper cylindrical shape. Similarly, embodiments are contemplated that would combine polymer and other securement means to maintain the helical structure.

DETAILED DESCRIPTION OF THE INVENTION

Figure 1:
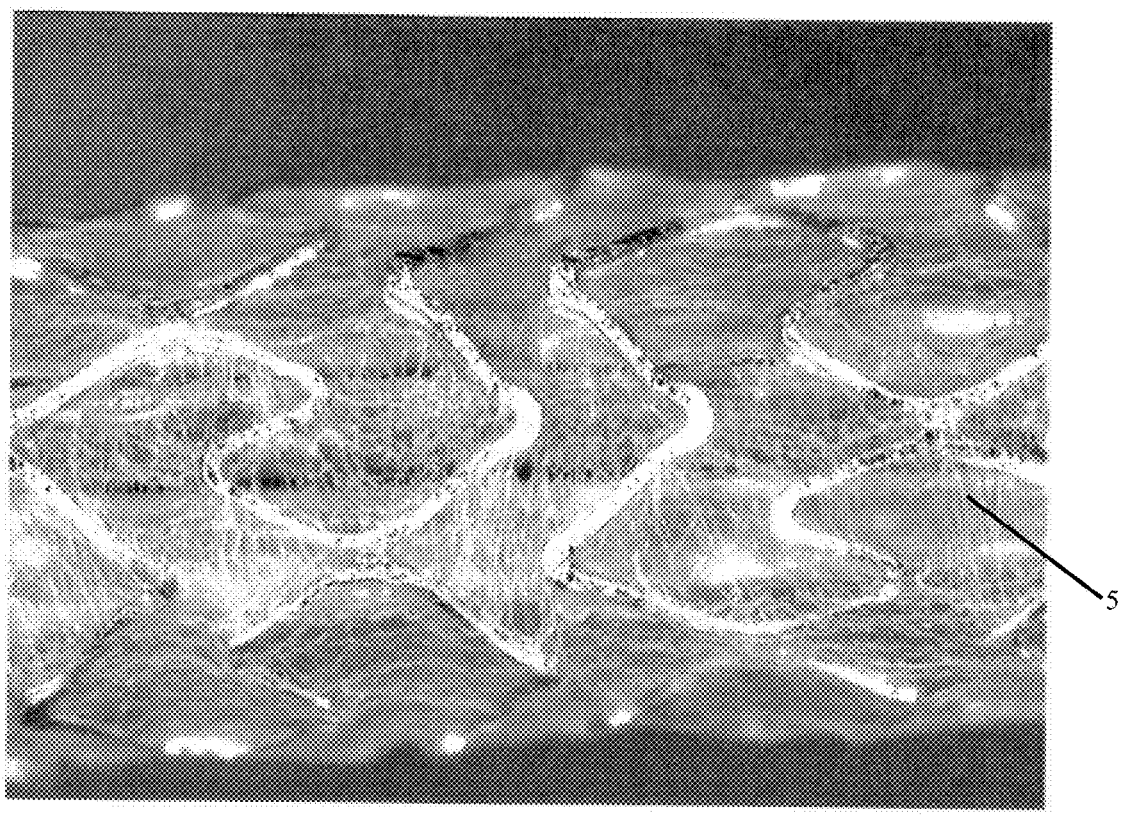
FIG. 1 illustrates a photomicrograph of stent members connected by a porous polymeric fiber structure.

This invention provides a new class of intraluminal prosthetic devices defined as helical hybrid stents. In particular, the stents of the present invention comprise a main stent component in the form of a helical tubular structure. The main stent component may be held in its coiled position by a second component, securing the helical coils into a tubular structure. The second component may be one or more of a variety of means for securing the main stent component in the tubular form. The second component may be, for example, weld points, interlocking means and/or a polymer. In one embodiment, the second component comprises a polymer or polymer fibers which wraps around or embeds itself in the coiled main stent component. The elastic range of the polymer fiber layer must be sufficient to allow expansion of the stent and maximal bending during and after implantation without reaching the elastic limit.

The stent of the present invention may be balloon expandable or self-expanding. When a balloon-expandable stent system is used to deliver the stent, the stent is mounted on the balloon and the catheter assembly is positioned at the implantation site. The balloon is then inflated, radially applying a force inside the stent and the stent is expanded to its expanded diameter. Alternatively, the stent may be self-expanding in which case a balloon is not needed to facilitate expansion and delivery of the stent.

By forming a stent with a single main stent component instead of separate components, the present invention provides for ease of manufacturing a whole stent structure without the necessity of forming multiple components and thereafter joining them to form a stent. The present invention also allows for the manufacturing of a stent formed of two or more simultaneously coiled main stent components which may or may not be of the same material or design, such that the windings of different ribbons may interchange, or alternate over the length of the stent. The present invention also allows for forming a stent from hard-to-weld materials, such as amorphous metal without the need to fix the individual rings.

The present invention relates to a stent comprising a continuous main stent component having side bands containing a periodic series of undulations that is helically arranged, for example, as a coil into a helical, tubular shape. The main stent component may be formed from one or more flat metal ribbons. Alternately, the main stent component may be formed as a tube wherein a helically coiled pattern has been etched or laser cut into it. In either case, the helical stent will have a pattern resembling a coiled ribbon or ribbons, wherein each ribbon comprises two or more parallel side bands each having an undulating pattern.

The side bands are joined together directly and/or through cross-struts. The main stent component may further comprise end bands, which have undulating bands extending at an angle from each end of the main stent component at an angle in the general direction of the side bands. The end bands each follow the circumferential axis of the helically coiled tubular structure. Optionally, the side bands of the ribbon may be tapered without resort to additional end bands. Both the end bands and tapering of the ends of the main stent component allow the ends of the finished stent to be straight; i.e., it allows the stent to form a right cylinder, with each of the ends of the cylindrical stent lying in a plane perpendicular to the longitudinal axis of the stent.

The cross-struts may be straight connectors or may have one or more loops between connection points to side bands and/or end bands. Further, individual cross-struts may connect an end band to an adjacent side band while other cross struts connect two adjacent end bands one to another or two adjacent side bands one to another.

The undulating patterns of the side bands and end bands are such that, in the helically coiled form of the ribbon, the adjacent side bands and/or end bands may be substantially parallel to one another. The undulating patterns are understood to have peaks and troughs. The troughs may be defined by points of connection to the cross-struts or to troughs of the adjacent-most side band or end band. The end bands are arranged at an angle such that the end bands extend about a circumferential axis of the helically coiled main stent component.

The end sections may be formed from the same ribbon which constitutes the side bands. The end sections support the helical coiled structure. Alternatively, the helical coils of the main stent component may be connected by separate end band elements aligned with the longitudinal direction of the stent or slanted relative to it.

The ribbon may be arranged to provide a cellular stent design. The helical main stent component can be any structure which provides a stored length to allow radial expansion. Example designs are described in, but not limited to, U.S. Pat. No. 6,723,119, which is incorporated herein in toto, by reference. Another example design is a stent pattern described in U.S. Pat. No. 7,141,062 ("'062"). The '062 stent comprises triangular cells, by which is meant a cell formed of three sections, each having a loop portion, and three associated points of their joining forming each cell. One or more rows of such cells may be assembled in a ribbon which may be helically coiled from two or more side bands to form a main stent component. Similarly, the cells in the stent described in U.S. Pat. No. 5,733,303 to Israel et al. ("'303") may be used for the main stent component but helically coiled. The '303 patent describes a stent having cells formed of four sections, each having a loop portion and four associated points of their joining forming each cell, also known as square cells. Such square cells may be formed with the side bands and cross struts of the helically coiled ribbon of the present invention. Each of these designs is expressly incorporated herein in toto by reference. Other similarly adaptable cellular stent designs known in the art are readily applicable to the helical stent of the present invention.

Employment of a light and porous or fiber polymeric material in the stents of the present invention provides several advantages. For example, a fibrous material may provide a longitudinal structure thereby enhancing the overall flexibility of the stent device. Such a material may be applied to a tubular stent in a continuous or non-continuous manner depending upon the particular needs of the structure contemplated. Polymeric material can form a porous fiber mesh that is a durable polymer. The longitudinal polymeric structure serves at least two functions. First, the longitudinal polymeric structure is more longitudinally flexible than a conventional metallic structure. Second, the polymeric material is a continuous structure with small inter-fiber distance and can be used as a matrix for eluting drug that would provide a more uniform elution bed. Another advantage of using these materials is that the continuous covering provided by the material after the stent is deployed in a vessel is believed to inhibit or decrease the risk of embolization. Yet another advantage is the prevention of "stent jail" phenomenon, or the complication of tracking into side branches covered by the stent. Further advantage is the high fatigue resistance of polymer structures with high elastic range.

The polymer layer can be disposed within interstices and/or embedded throughout the stent. The polymer layer may secure portions of the stent structure or may fully envelop the entire stent. The polymer layer is a biocompatible material. Biocompatible material may be a durable polymer, such as polyesters, polyanhydrides, polyethylenes, polyorthoesters, polyphosphazenes, polyurethane, polycarbonate urethane, silicones, polyolefins, polyamides, polycaprolactams, polyimides, polyvinyl alcohols, acrylic polymers and copolymers, polyethers, celluiosics and any of their combinations in blends or as copolymers. Of particular use may be silicone backbone-modified polycarbonate urethane and/or expanded polytetrafluoroethylene (ePTFE).

FIG. 1 shows a photomicrograph of an exemplary stent illustrating stent members connected by a porous polymer layer. The stent of FIG. 1 is connected by a polymer layer 5 represented here as a porous longitudinal structure along a longitudinal axis of the stent. Illustrated here, the polymer layer 5 is a porous durable fiber mesh. The polymer layer 5 provides a continuous structure having small inter-fiber distances and forming a matrix. This matrix may be used for eluting a drug and may provide a uniform elution bed over conventional methods. In addition, the polymer layer 5 may function to hold the main stent component in a tubular shape and to prevent unwinding upon expansion and flexing. In addition, the polymer layer 5 enables longitudinal flexibility to the stent structure. FIG. 1 shows a photomicrograph of an exemplary stent illustrating stent members connected by a porous polymer layer. The stent of FIG. 1 is connected by a polymer layer represented here as a porous longitudinal structure along a longitudinal axis of the stent. Illustrated here, the polymer layer is a porous durable fiber mesh. The polymer layer provides a continuous structure having small inter-fiber distances and forming a matrix. This matrix may be used for eluting a drug and may provide a uniform elution bed over conventional methods. In addition, the polymer layer may function to hold the main stent component in a tubular shape and to prevent unwinding upon expansion and flexing. In addition, the polymer layer enables longitudinal flexibility to the stent structure.

The longitudinal structure of the biocompatible polymer layer may be porous or it may be formed as a tube with fenestrations or a series of fibers with spaces between them, to promote growth of neo-intima that will cover the stent and secure it in position. Fenestrations may also promote better stabilization of the stent. The shape of fenestration can be made in any desired size, shape or quantity.

Figure 2:
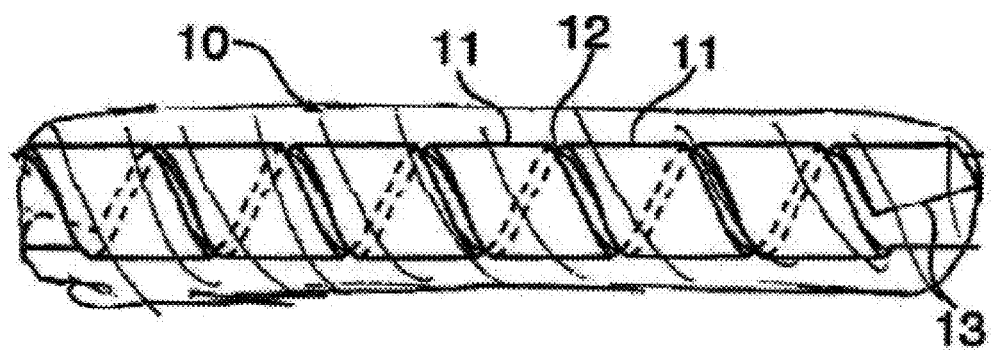
FIG. 2 illustrates stent having a schematic helical component connected by a fiber polymeric structure.

FIG. 2 shows an example helically coiled ribbon 12 disposed in a polymer layer such as a porous fiber mesh 10. As shown in FIG. 2, the stent is formed as a helically wound ribbon having ends 13 and coils 11. Depending on the embodiment, the coils 11 of the ribbon 12 are relatively resistant to longitudinal displacement or tilting because of the width of the ribbon 12. The mesh 10, although allowing longitudinal flexibility of the stent, further provides support to the stent to resist longitudinal displacement or tilting. The ribbon 12 is designed to have a helical tubular shape.

Figure 3:
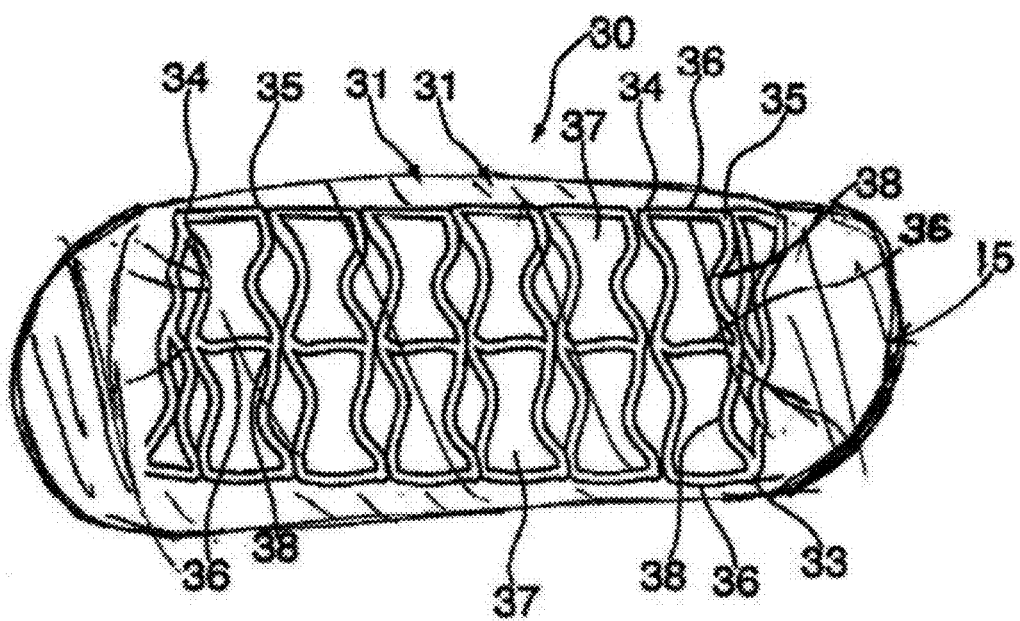
FIG. 3 illustrates one embodiment of a main stent component connected by a fiber polymeric structure.

FIG. 3 shows a serpentine coiled ladder stent 30 constructed in accordance with the invention. The serpentine coiled ladder stent 30 in FIG. 3 is shown having a porous fiber mesh 15 disposed about the stent.

The serpentine coiled ladder stent 30 embodiment illustrated in FIG. 3 is configured as a helical stent in which the coils are formed from a helical strip of cells 37, wherein the sides of the cells 37 are serpentine or contain undulations. The stent in this illustration is comprised of a strip helically wound into a series of helical coils 31, wherein the main stent component is formed of two side bands 34, 35 connected to each other, for example by a series of cross struts 36. Each side band 34, 35 is formed in a serpentine pattern comprising a series of undulations 38. Upon expansion of the stent, the undulations 38 of the side bands 34, 35 open to increase the length of each of the individual cells 37 in the helical direction. Thus, lengthening the strip in the helical direction permits the stent 30 to expand without any significant unwinding of the strip, or foreshortening. In the unexpanded state, the side bands collapse to form a serpentine continuum.

In the illustrated embodiment of FIG. 3, the cross struts 36 joining the side bands 34, 35 to each other are straight and extend in a direction generally perpendicular to the helical direction in which the strip is wound. Alternatively, the cross struts may have one or more bends, and/or they may extend between the two side bands at other angles. In the illustrated embodiment, the cross struts 36 join oppositely facing undulations 38 on the side bands 34, 35, and they are attached to the side bands 34, 35 at every second undulation 38. Alternatively, the cross struts 36 may be joined in other places, and may occur with more or less frequency, without departing from the general concept of the invention. The side bands 34, 35 and the cross struts 36 form the perimeter of each cell. The stent alternatively may be formed without cross struts 36, by having, for example, the two serpentine side bands 34, 35 periodically joined directly to each other at adjacent points.

Furthermore, as shown in FIG. 3, the ends 33 of the serpentine main stent component may be tapered. The tapering of the ends 33 of the main stent component allows the ends of finished stent to be straight, i.e., it allows the stent to take the form of a right cylinder, with each of the ends of the cylindrical stent lying in a plane perpendicular to the longitudinal axis of the stent. The ends 33 of the main stent component may be joined to respective adjacent windings 31 using the porous fiber mesh 15 to join ends 33, for example when made from an amorphous metal.

Figure 4:
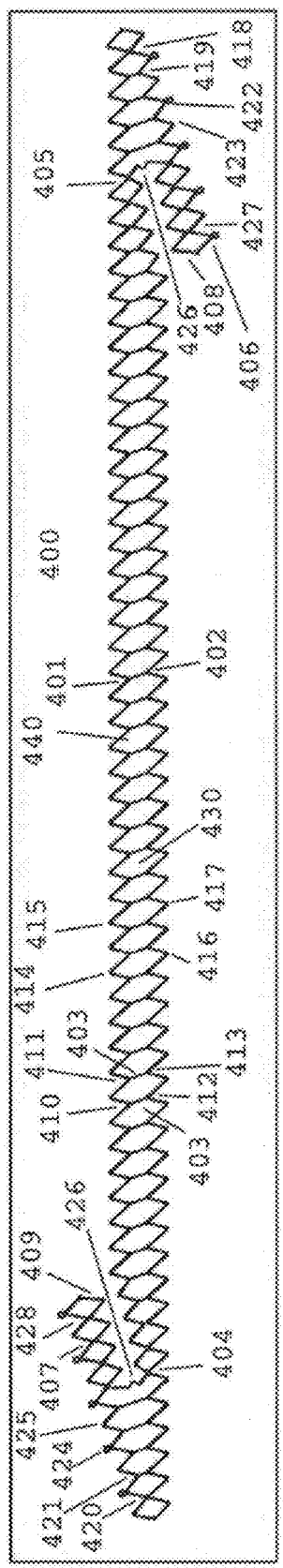
FIG. 4 illustrates a flat ribbon main stent component formed according to one embodiment of the invention.

FIG. 4 illustrates an embodiment of the invention wherein the main stent component is shown in the flatten ribbon form. The main stent component 400 is shown in an uncoiled state, i.e., flat. As depicted in FIG. 4, the main stent component 400 has an undulating design in the longitudinal direction. The undulating design comprises a first side band 401 having an undulating shape and a second side band 402 having an undulating shape. The first side band 401 and second side band 402 are arranged along a generally parallel orientation except at either end of the side bands where the first side band tapers toward the second side band and the second side band tapers toward the first side band. Accordingly, when the main stent component 400 is laid flat as depicted in FIG. 4, the undulations of the first side band 401 comprise troughs (e.g., 410, 411) that face toward the second side band 402 and peaks (e.g., 414, 415) that face away from the second side band 402. Similarly, the undulations of the second side band 402 comprise troughs (e.g., 412, 413) that face toward the first side band 401 and peaks (e.g., 416, 417) that face away from the first side band 401. The first side band 401 and second side band 402 are connected to each other by a plurality of first cross struts 403 to form cells 440. In particular, for example, at least one trough (e.g., 410) of the first side band 401 is connected to a corresponding trough (e.g., 412) of the second side band 402 via a first cross strut 403. Thus, a series of cells are formed, each cell defined individually by the joining of the adjacent side bands to form an enclosed space by cross-struts. For example, in FIG. 4, a cell is defined by the portion of the first side band between troughs 410 and 411, the portion of the second side band between troughs 412 and 413 and the first cross-struts 403 respectively connecting troughs 410 and 412 and inner peaks 411 and 413.

In FIG. 4, the first cross struts 403 connect first side band 401 and second side band 402 at regular intervals, in particular at adjacent troughs, thereby forming cells, e.g., 430. In alternative embodiments, the number of first cross struts 403 may differ from that illustrated in FIG. 4. For example, the first cross-struts 403 may connect the first band 401 and second band 402 at regular intervals at, for example, every second trough, or every third trough, or every fourth trough, etc., thereby making larger cells. In still other embodiments, the first cross struts 403 may connect the first side band 401 and second side band 402 at varying intervals, for example, the varying interval pattern may be: adjacent trough, third trough, adjacent trough, fourth trough, adjacent trough, third trough, etc. (not shown), or another pattern, as may be appropriate for a particular use, thereby making a variety of differently sized cells along the main stent component. The first cross-struts 403 may each have the same width relative to each other and to the side bands 401, 402, as shown in FIG. 4. Alternatively, the first cross-struts 403 may have a different width from the first and second side bands 401, 402, or a different width from each other, as appropriate for a particular use. In addition, first cross-struts 403 may comprise a straight member or may contain one or more loops, thereby forming square cells similar to those taught by the '303 patent or triangular cells as taught in the '062 patent. The cross struts may connect adjacent or offset troughs of the first and second side bands 401, 402. As shown in FIG. 4, differently shaped cross-struts, or no cross-struts may alternatively be employed in a single stent design depending on the particular use of the stent so that a stent having different cell shapes may be formed.

The main stent component 400 in the embodiment depicted in FIG. 4 tapers at each end. In particular, the length of the cross struts 403 shorten toward each end of the main stent component 400, so that the first and second bands 401, 402 become closer together and eventually are connected directly at points of connection 404 and 405. Alternatively, in embodiments without cross struts, the undulations may become more shallow to create a tapered end on the flattened ribbon of the main stent component.

Extending from the end of either side band 401 and 402 in FIG. 4 are end bands 406 and 407. Thus, a first end band 406 extends from the end of the first side band 401 in a direction offset from the general direction of the first side band 401. A second end band 407 extends from the end of the second side band 402 in a general direction offset from the general direction of the second side band 402 and opposite the first end band. The first end band 406 and second end band 407 each have an undulating pattern. The first end band 406 has troughs (e.g. 418, 419) that face toward the first side band 401 and peaks (e.g. 422, 423) that face away from the first side band 401. Likewise, the second end band 407 has troughs (e.g. 420, 421) that face toward the second side band and peaks (e.g. 424, 425) that face away from the second side band 402. The first end band 406 connects directly to the first side band 401 at, e.g., trough 418; however, as the first end band 406 angularly extends away from the first side band, second cross-struts 426 connect the first end band 406 to the first side band 401. Likewise, the second end band 407 connects directly to the second side band 402 at, e.g., trough 420; however, as the second end band 407 angularly extends away from the second side band, second cross-struts 426 connect the second end band 407 to the second side band 402. As depicted in FIG. 4, the second cross struts 426 may contain one or more loops between points of connection with adjacent end bands and/or side bands. The peaks of the first end band 406 and second end band 407 optionally may have additional circular structures extending from the peaks (e.g. 423, 424) as depicted by FIG. 4.

In addition, a third end band 408 is arranged generally parallel to first end band 406, with troughs facing each other and connecting directly, e.g. 427, to said first end band. A fourth end band 409 is arranged generally parallel to second end band 407, with troughs facing each other and connecting directly, e.g. 428, to said second end band. The third end band 408 and fourth end band 409 each have an undulating pattern.

Figure 5:
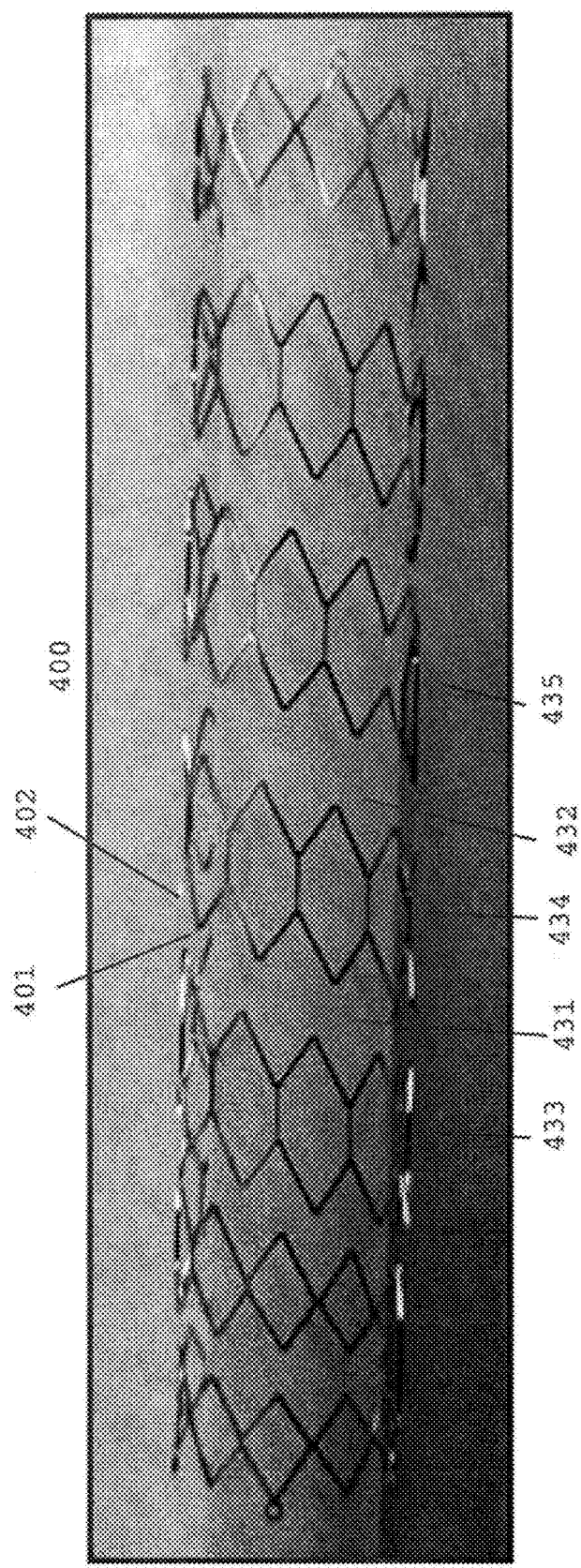
FIG. 5 illustrates a helical main stent component according to the invention having variable distances between helical coils.

FIG. 5 illustrates a helically coiled stent wherein the main stent component 400 forms a tubular structure and the end bands of the ribbon secure the ends of the tubular structure. The undulating design of the main stent component 400 forms a helical, tubular structure, in which the coils of the helix self-arrange to create variable and/or uniform spacing along the longitudinal axis of the tubular structure, e.g. 431, 432, between helical cycles, e.g. 433, 434, 435, as depicted in FIG. 5. Because the stent 400 forms a helix, the first side band 401 and the second side band 402 of the ribbon, may be spaced apart to various extents.

Figure 6:
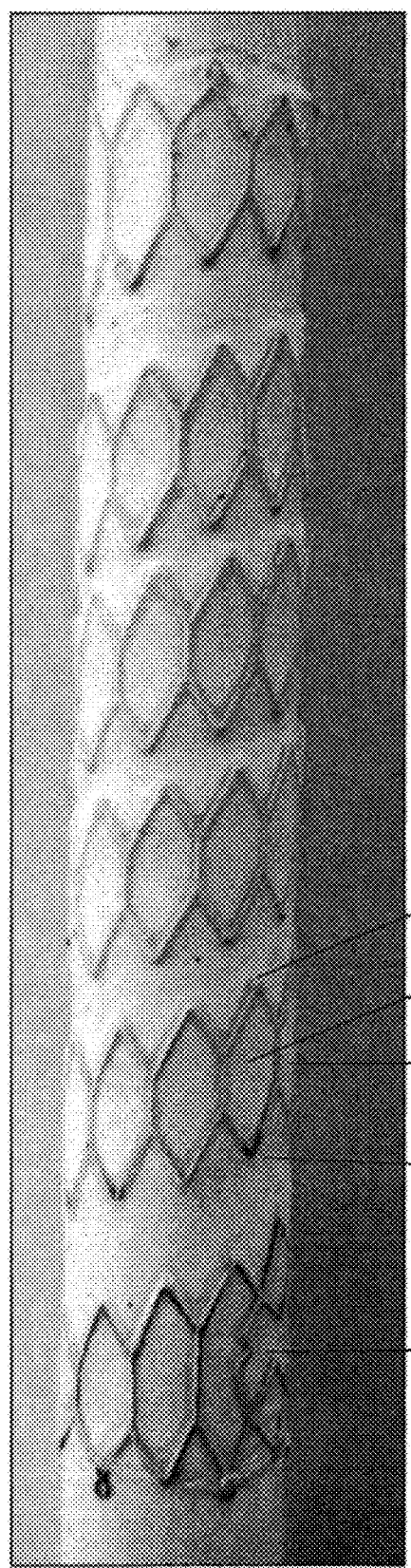
FIG. 6 illustrates another embodiment of the invention having a helical main stent component having side bands and end bands, detailing varying cross struts, and embedded in a polymer.

The helical main stent component 500 may also be secured by embedding the tubular structure in a longitudinal polymer layer as in FIG. 5 and/or FIG. 6, rather than by locking mechanisms or welding alone. The longitudinal polymer layer comprises a biocompatible material. The stent in FIG. 6 is rotated slightly compared to that in FIG. 5 so that the second cross-strut 426 having a loop is visible. Also identified are the first band 401, the second band 402, a first cross strut 403, and a cell 430.

Figure 7:
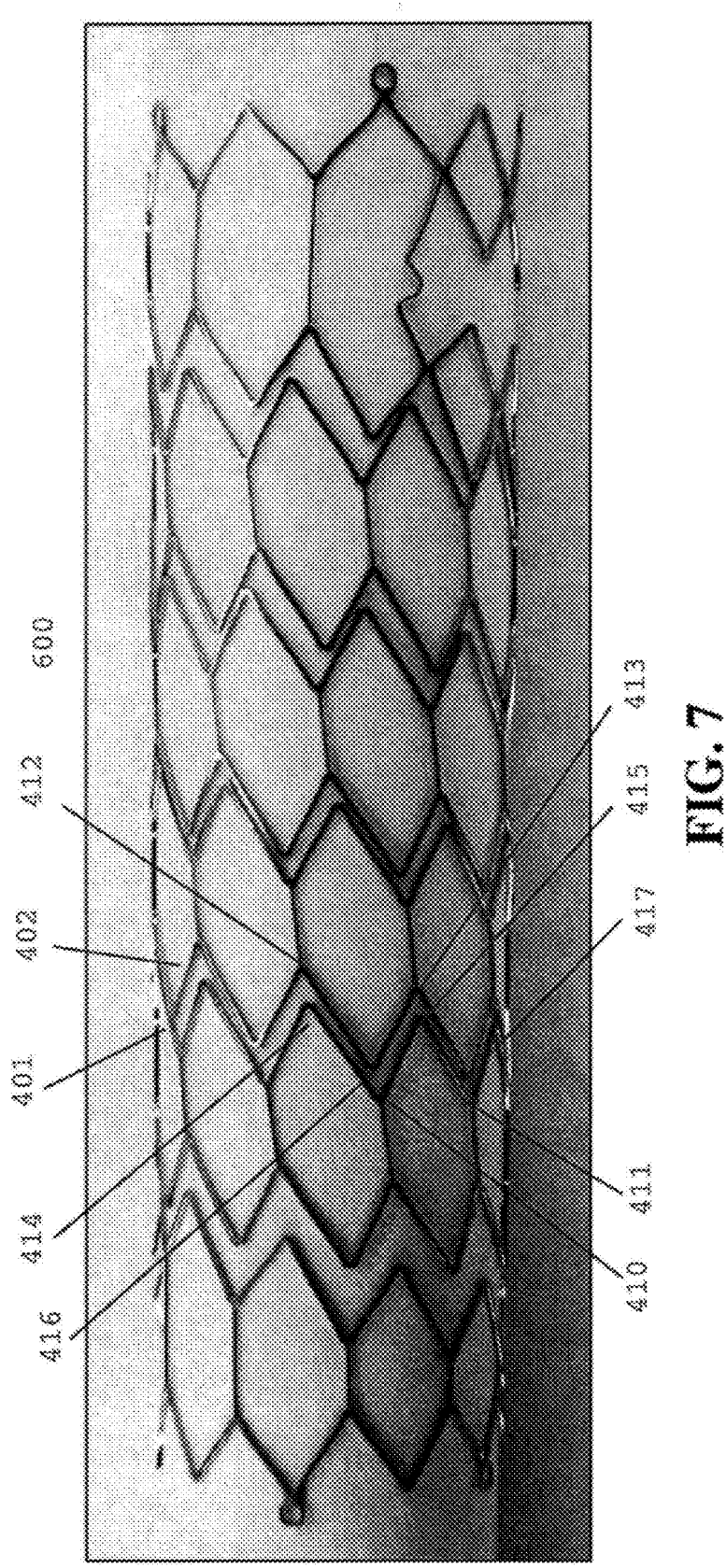
FIG. 7 illustrates yet another embodiment of the invention wherein the helical main stent component has its coils nestled into one another.

FIG. 7 illustrates a stent according to the invention wherein the helical coils are positioned so that little or no substantial longitudinal space exists between cycles of the helical coils. That is, as illustrated by FIG. 7, the peaks (e.g. 414, 415) of the first side band 401 nestle into the circumferential area created by the peaks (e.g. 416, 417) of the second side band such that the peaks 414, 415 of the first side band 401 approach the troughs 412, 413 of the second side band 402; yet, the first side band 401 remains substantially parallel to the second side band 402. Likewise, the peaks (e.g. 416, 417) of the second side band 402 nestle into the circumferential area created by the peaks (e.g. 414, 415) such that the peaks 416, 417 of the second side band 402 are in close proximity to the troughs 410, 411 of the first side band 401. It may be desirable to position the nestled side bands so that no direct contact occurs between first side band 401 and second side band 402. Because the first side band 401 and the second side band 402 have substantially similar design, the first side band 401 and the second side band 402 can approach one another in this fashion over the entire length of the formed stent. In this manner, the first side band 401 and the second side band 402 may be described as nestled to one another. The stent of FIG. 7 has the additional advantage that the nestled pattern of adjacent first and second side bands minimizes the unsupported areas of the vessel wall and/or polymer layer to prevent sagging of the polymer layer into the lumen upon expansion without any loss of flexibility to the stent. In addition, the nestling of the helical coils separately facilitates the maintenance of the structure in the tubular form.

When the stent of the invention comprises an amorphous metal alloy, it provides the further advantage of enhanced corrosion resistance, resistance to unwanted permanent deformation and higher strength for a given metal thickness. Stents of the present invention comprising amorphous metal alloys exhibit significantly lower conductance or are non-conductive, compared to their crystalline or polycrystalline counterparts. Many medical uses for stents can benefit from such enhanced physical and chemical properties. One embodiment of this invention contemplates intraluminal prosthetic devices comprising at least one amorphous metal alloy combined with components made of other materials, with biocompatible materials being required. This embodiment of the invention may contain one or more amorphous metal alloys. Such alloys provide improved tensile strength, elastic deformation properties, and reduced corrosion potential to the devices.

Amorphous metal alloys, also known as metallic glasses, are disordered metal alloys that do not have long-range crystal structure. Many different amorphous metal alloy compositions are known, including binary, ternary, quaternary, and even quinary alloys. Amorphous metal alloys and their properties have been the subject of numerous reviews (see, for example, *Amorphous Metal Alloys*, edited by F. E. Luborsky, Butterworth & Co, 1983, and references therein). In certain embodiments, the amorphous metal alloys may comprise a metalloid, non-limiting examples of which include silicon, boron, and phosphorus. One possible amorphous metal alloy is an Fe—Cr—B—P alloy. Many other similar alloys are suitable and known to one of ordinary skill in the art.

The stents of the present invention may contain amorphous metal alloys made in a continuous hot extrusion process, as described herein, which possess physical and chemical properties that make them attractive candidates for use in medical devices. For example, amorphous metal alloys may have a tensile strength that is up to ten-fold higher than that of their conventional crystalline or polycrystalline metal counterparts. Also, amorphous metal alloys may have a ten-fold wider elastic range, i.e., range of local strain before permanent deformation occurs. These are important features in medical devices to provide an extended fatigue-resistant lifespan for devices that are subjected to repeated deformations in the body. In addition, these features allow production of smaller or thinner devices that are as strong as their bulkier conventional counterparts.

In other embodiments, the device may contain one or more non-amorphous metals. For example, the device may have components constructed of stainless steel, cobalt chromium ("CoCr"), NiTi or other known materials. With regard to NiTi, the contemplated component may be formed by etching a flat sheet of NiTi into the desired pattern. The flat sheet is formed by rolling the etched sheet into a tubular shape, and optionally welding the edges of the sheet together to form a tubular stent. The details of this method, which has certain advantages, are disclosed in U.S. Pat. Nos. 5,836,964 and 5,997,973, which are hereby expressly incorporated by reference. Other methods known to those of skill in the art such as laser cutting a tube or etching a tube may also be used to construct a stent of the present invention. A NiTi stent, for example, may be heat treated, as known by those skilled in the art, to take advantage of the shape memory characteristics and/or its super-elasticity.

The amorphous metal alloy or other non-amorphous metal components of this invention may also be combined or assembled with other components, either amorphous metal or otherwise, in order to form intraluminal stents. For example, the amorphous metal alloy or other non-amorphous metal components may be combined with a polymer layer such as a biocompatible polymer, a therapeutic agent (e.g., a healing promoter as described herein) or another metal or metal alloy article (having either a crystalline or amorphous microstructure).

The method of combining or joining the amorphous metal alloy or other non-amorphous metal components to other components can be achieved using methods that are well known in the art. Particularly in the case of non-amorphous metals, the helically coiled main stent component may be secured or otherwise intertwined or joined at the ends to the adjacent helical coils. For example, a biocompatible polymer layer covering all or part of the main stent component may be used to secure the helical coils in its tubular shape for positioning and expansion in the lumen. Other non-limiting examples of securement methods including physical joining (e.g., braiding, weaving, crimping, tying, and press-fitting) and joining by adhesive methods (e.g., gluing, dip coating, and spray coating). Combinations of these methods are also contemplated by this invention.

As a further advantage of the invention, the biocompatible structure may be embedded with drug that will inhibit or decrease cell proliferation or will reduce restenosis. Non-limiting examples of such drugs include for example sirolimus, rapamycin, everolimus and paclitaxol, and analogs of these. In addition, the stent may be treated to have active or passive surface components such as drugs that will be advantageous for a longer time after the stent is embedded in the vessel wall.

Various methods of making amorphous metal alloys are known in the art, examples of which are described further below. While preferred embodiments may be shown and described, various modifications and substitutions may be made without departing from the spirit and scope of the present invention. Accordingly, it is to be understood that the present invention is described herein by way of example, and not by limitation.

Methods of Making Amorphous Metal Alloys

Many different methods may be employed to form amorphous metal alloys. A preferred method of producing medical devices according to the present invention uses a process generally known as heat extrusion, with the typical product being a continuous article such as a wire or a strip. The process does not involve additives commonly used in the bulk process that can render the amorphous metal alloy non-biocompatible and even toxic. Thus, the process can produce highly biocompatible materials. In preferred embodiments, the continuous amorphous metal alloy articles are fabricated by a type of heat extrusion known in the art as chill block melt spinning. Two common chill block melt spinning techniques that produce amorphous metal alloy articles suitable for the medical devices of the present invention are free jet melt-spinning and planar flow casting. In the free jet process, molten alloy is ejected under gas pressure from a nozzle to form a free melt jet that impinges on a substrate surface. In the planar flow method, the melt ejection crucible is held close to a moving substrate surface, which causes the melt to be simultaneously in contact with the nozzle and the moving substrate. This entrained melt flow dampens perturbations of the melt stream and thereby improves ribbon uniformity. (See e.g., Liebermann, H. et al., "Technology of Amorphous Alloys" *Chemtech*, June 1987). Appropriate substrate surfaces for these techniques include the insides of drums or wheels, the outside of wheels, between twin rollers, and on belts, as is well known in the art.

Suitable planar flow casting and free jet melt spinning methods for producing amorphous metal alloy components for the medical devices of this invention are described in U.S. Pat. Nos. 4,142,571; 4,281,706; 4,489,773, and 5,381,856; all of which are hereby incorporated by reference in their entirety. For example, the planar flow casting process may comprise the steps of heating an alloy in a reservoir to a temperature 50-100° C. above its melting temperature to form a molten alloy, forcing the molten alloy through an orifice by pressurizing the reservoir to a pressure of about 0.5-2.0 psig, and impinging the molten alloy onto a chill substrate, wherein the surface of the chill substrate moves past the orifice at a speed of between 300-1600 meters/minute and is located between 0.03 to 1 millimeter from the orifice. In embodiments involving free-jet melt spinning, the process may comprise the steps of heating an alloy in a reservoir to a temperature above the melting point of the alloy, ejecting the molten alloy through an orifice in the reservoir to form a melt stream with a velocity between 1-10 meters/second, and impinging the melt stream onto a chill substrate, wherein a surface of the chill substrate moves past the orifice at a speed of between 12-50 meters/second.

Besides quenching molten metal (e.g., chill block melt spinning), amorphous metal alloys can be formed by sputter-depositing metals onto a substrate, ion-implantation, and solid-phase reaction. Each of these methods has its advantages and disadvantages. The choice of a particular method of fabrication depends on many variables, such as process compatibility and desired end use of the amorphous metal alloy article.

In some embodiments of the invention, amorphous metal alloy components for stents may be used. These components may be provided in a variety of ways. For example, the component may be produced by machining or processing amorphous metal alloy stock (e.g., a wire, ribbon, rod, tube, disk, and the like). Amorphous metal alloy stock made by chill block melt spinning can be used for such purposes.

It should be understood that the above description is only representative of illustrative examples of embodiments. For the reader's convenience, the above description has focused on a representative sample of possible embodiments, a sample that teaches the principles of the invention. Other embodiments may result from a different combination of portions of different embodiments. The description has not attempted to exhaustively enumerate all possible variations.

The invention claimed is:

1. A helical stent comprising a helical main stent component and a polymer material, wherein said main stent component comprises:
   a) a first side band having a first end and a second end, and a second side band having a first end and a second end, wherein the first and second side bands each have an undulating pattern, wherein the first end of the first side band tapers to narrow and connect to the second side band, and the first end of the second side band tapers to narrow and connect to the first side band; and b) a first end band comprising a series of struts forming a first undulation, said first end band having a first end and a second end, wherein the first end of said first end band is connected to the first end of the first side band, and a second end band comprising a series of struts forming a second undulation, said second end band having a first end and a second end, wherein the first end of the second end band is connected to the first end of the second side band.

2. The stent according to claim 1, wherein the first and second end bands may include one or more of hooks, polymers and welds to secure the first and second end bands in a helical shape.

3. The stent according to claim 1 wherein at least one of said side bands forms a ring around the circumference of the helical main stent component.

4. The stent according to claim 3 wherein the ring occurs at the end of the stent upon helically winding the main stent component.

5. The stent according to claim 1, wherein the first side band and second side band are connected to form a plurality of cells.

6. The stent according to claim 5, wherein at least one of said cells has a different size from at least one other of said cells.

7. The stent according to claim 5, wherein a first portion of the first side band is connected to a first portion of the second side band by cross struts.

8. The stent according to claim 7, wherein a second portion of the first side band is directly connected to a second portion of the second side band.

9. The stent according to claim 8, wherein the second portions are located at first and second ends of the first and second bands.

10. The stent according to claim 1 wherein the polymer material is a fiber mesh.

11. The stent according to claim 1 wherein the polymer material is a porous material.

12. The stent according to claim 1 wherein the polymer material is a durable material.

13. The stent according to claim 1, wherein the polymer material extends across the entire length of the main stent component.

14. The stent according to claim 1, wherein the polymer material covers an end of the main stent component.

15. The stent according to claim 1, wherein the polymer material has fenestrations.

16. The stent according to claim 1, wherein the polymer material is ePTFE.

17. The stent according to claim 1, wherein the polymer material provides longitudinal rigidity to the stent.

18. The stent according to claim 1, wherein the polymer material provides structural support for the stent.

19. The stent according to claim 1, wherein said first side band directly connects to the second side band and wherein said second side band directly connects to the first side band.

20. A main stent component comprising:
a) a first side band having a first end and a second end, and a second side band having a first end and a second end, wherein the first and second side bands each have an undulating pattern, wherein the first end of the first side band tapers to narrow and connect to the second side band, and the first end of the second side band tapers to narrow and connect to the first side band, wherein the main stent component is configured to be helically wound;

b) a first end band comprising a series of struts forming a first undulation, said first end band having a first end and a second end, wherein the first end of said first end band is connected to the first end of the first side band, and a second end band comprising a series of struts forming a second undulation, said second end band having a first end and a second end, wherein the first end of said second end band is connected to the first end of the second side band.

21. The stent according to claim 20, wherein said first side band directly connects to the second side band and wherein said second side band directly connects to the first side band.

22. A method of making a helical stent according to claim 1, said method comprising the steps of:
a) aligning the second end of the first end band with the first hook of the helical main stent component;
b) connecting said second end of the first end band with the first hook;
c) aligning the second end of the second end band with the second hook;
d) connecting said second end of the second end band with the second hook; and
e) applying said polymer material.

23. The method according to claim 22, further comprising the step of welding the first hook to the second end of the first end band.

24. The method according to claim 22, further comprising the step of welding the second hook to the second end of the second end band.

25. The method according to claim 22, further comprising the step of applying said polymer material, wherein said polymer is affixed to the main stent component by electrospinning.

* * * * *